United States Patent
Dimitrievska et al.

(10) Patent No.: US 9,981,066 B2
(45) Date of Patent: May 29, 2018

(54) ANTI-THROMBOGENIC GRAFTS

(71) Applicant: Yale University, New Haven, CT (US)

(72) Inventors: Sashka Dimitrievska, Branford, CT (US); Laura Niklason, Greenwich, CT (US)

(73) Assignee: Yale University, New Haven, CT (US)

(*) Notice: Subject to any disclaimer, the term of this patent is extended or adjusted under 35 U.S.C. 154(b) by 0 days. days.

(21) Appl. No.: 14/783,897

(22) PCT Filed: May 19, 2014

(86) PCT No.: PCT/US2014/038597
§ 371 (c)(1),
(2) Date: Oct. 12, 2015

(87) PCT Pub. No.: WO2014/189835
PCT Pub. Date: Nov. 27, 2014

(65) Prior Publication Data
US 2016/0058913 A1 Mar. 3, 2016

Related U.S. Application Data

(60) Provisional application No. 61/825,256, filed on May 20, 2013.

(51) Int. Cl.
*A61L 27/50* (2006.01)
*A61K 31/727* (2006.01)
(Continued)

(52) U.S. Cl.
CPC .......... *A61L 27/507* (2013.01); *A61K 31/727* (2013.01); *A61L 27/34* (2013.01); *A61L 27/3625* (2013.01); *A61L 27/52* (2013.01); *A61L 27/54* (2013.01); *A61L 33/0011* (2013.01); *A61L 33/0029* (2013.01);
(Continued)

(58) Field of Classification Search
None
See application file for complete search history.

(56) References Cited

U.S. PATENT DOCUMENTS

| | | | |
|---|---|---|---|
| 6,884,788 B2* | 4/2005 | Bulpitt | C07C 323/25 514/54 |
| 2001/0044654 A1* | 11/2001 | Chen | A61L 27/3625 623/1.41 |

(Continued)

OTHER PUBLICATIONS

European Search Report for European Patent Application No. 14800261.1 dated Dec. 20, 2016.

(Continued)

*Primary Examiner* — Carlos A Azpuru
*Assistant Examiner* — Casey S Hagopian
(74) *Attorney, Agent, or Firm* — Saul Ewing Arnstein & Lehr LLP; Kathryn Doyle

(57) ABSTRACT

The present invention provides anti-thrombogenic compositions, including anti-thrombogenic vascular grafts. In certain embodiments, the compositions comprise decellularized tissue coated with an anti-thrombogenic coating. The present invention also provides methods of preparing anti-thrombogenic compositions and methods of treatment comprising implanting the anti-thrombogenic compositions into a subject in need thereof.

7 Claims, 21 Drawing Sheets

(51) Int. Cl.

| | | |
|---|---|---|
| *A61L 27/34* | (2006.01) | |
| *A61L 27/36* | (2006.01) | |
| *A61L 27/54* | (2006.01) | |
| *A61L 33/00* | (2006.01) | |
| *A61L 27/52* | (2006.01) | |
| *A61L 33/08* | (2006.01) | |
| *A61K 35/44* | (2015.01) | |
| *B05D 7/00* | (2006.01) | |

(52) U.S. Cl.
CPC ........... *A61L 33/0064* (2013.01); *A61L 33/08* (2013.01); *B05D 7/54* (2013.01); *A61K 35/44* (2013.01); *A61L 2300/236* (2013.01); *A61L 2300/42* (2013.01); *A61L 2300/608* (2013.01); *A61L 2420/02* (2013.01); *A61L 2420/08* (2013.01); *A61L 2430/40* (2013.01)

(56) References Cited

U.S. PATENT DOCUMENTS

| | | | |
|---|---|---|---|
| 2003/0161938 A1 | 8/2003 | Johnson | |
| 2004/0048796 A1* | 3/2004 | Hariri | A61K 35/50 424/423 |
| 2013/0023507 A1* | 1/2013 | Hossainy | A61K 31/727 514/179 |

OTHER PUBLICATIONS

PCT International Search Report and Written Opinion for PCT International Application No. PCT/US2014/038597 dated Dec. 11, 2014.

Hennink, et al., "Novel crosslinking methods to design hydrogels", Adv Drug Deliv Rev. 54(1), Jan. 17, 2002, 13-36.

Hill-West, et al., "Inhibition of thrombosis and intimal thickening by in situ photopolymerization of thin hydrogel barriers", Proc Natl Acad Sci U S A. 91(13), Jun. 21, 1994, 5967-5971.

Hoffman, "Hydrogels for biomedical applications", Adv Drug Deliv Rev. 54(1), Jan. 17, 2002, 3-12.

Hwang, et al., "Chondrogenic differentiation of human embryonic stem cell-derived cells in arginine-glycine-aspartate-modified hydrogels", Tissue Eng. 12(9), Sep. 2006, 2695-2706.

Ifkovits, et al., "Review: photopolymerizable and degradable biomaterials for tissue engineering applications", Tissue Eng. 13(10), Oct. 2007, 2369-2385.

Nguyen, et al., "Photopolymerizable hydrogels for tissue engineering applications", Biomaterials. 23(22), Nov. 2002, 4307-4314.

Shin, et al., "Biomimetic materials for tissue engineering", Biomaterials. 24(24), Nov. 2003, 4353-4364.

* cited by examiner

Decellularized Control

Hyaluronan-heparin coated

Layer 1 – Hyaluronic Acid
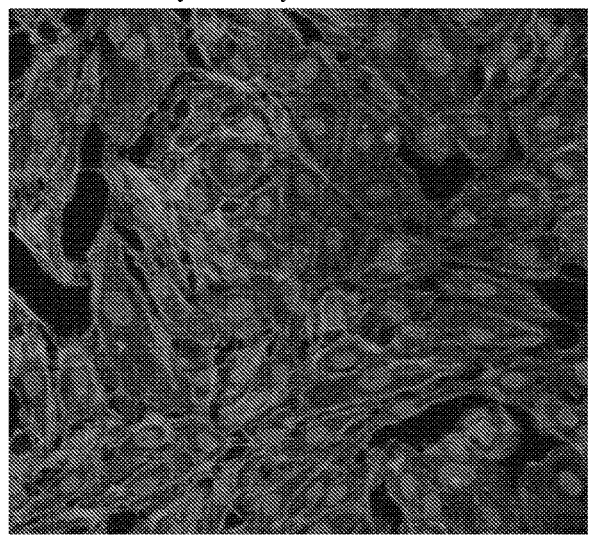
Thiol-modified Hyaluronic acid 4
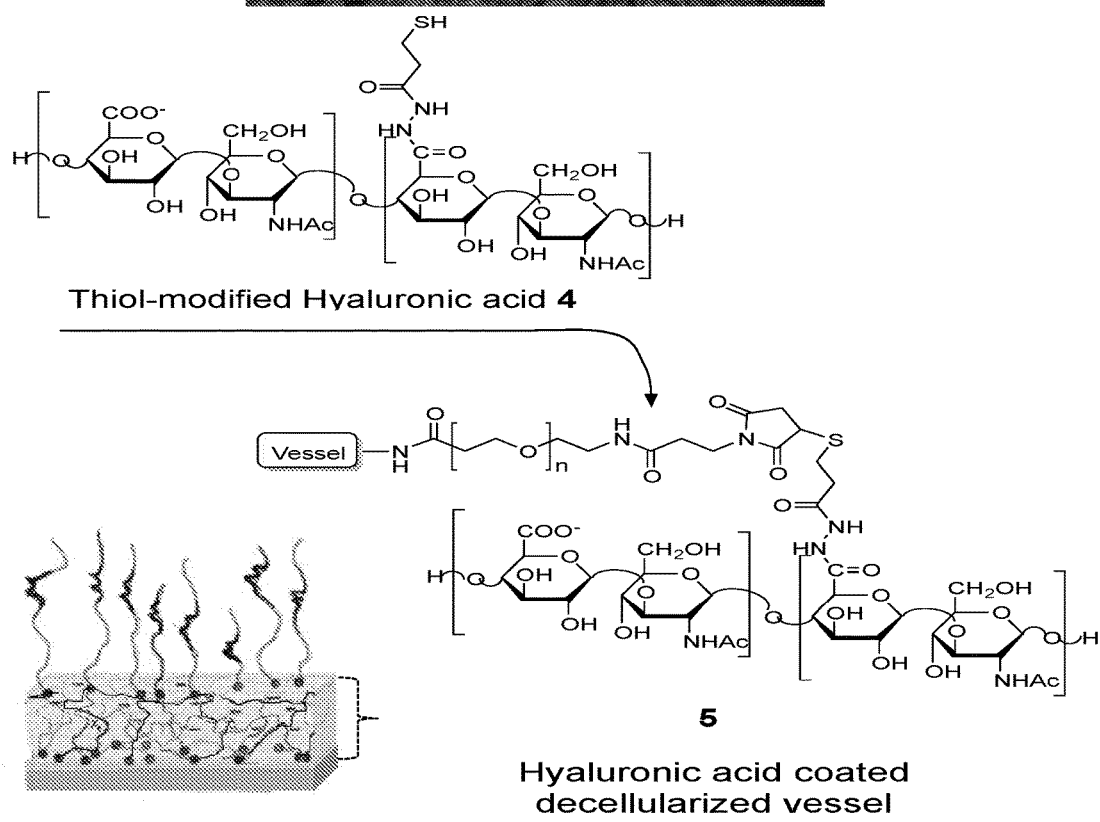
Hyaluronic acid coated decellularized vessel
Figure 13, continued

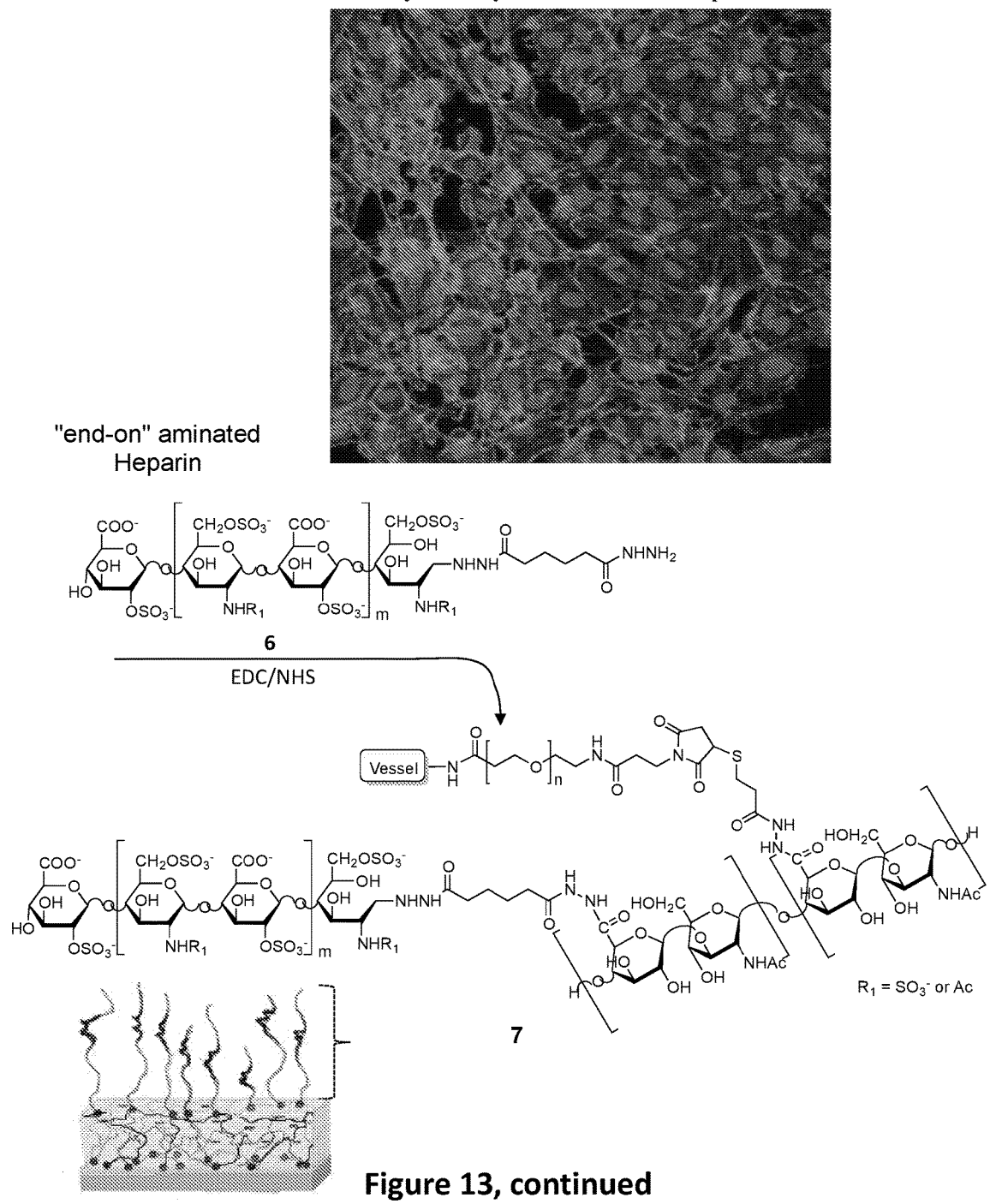
Figure 13, continued

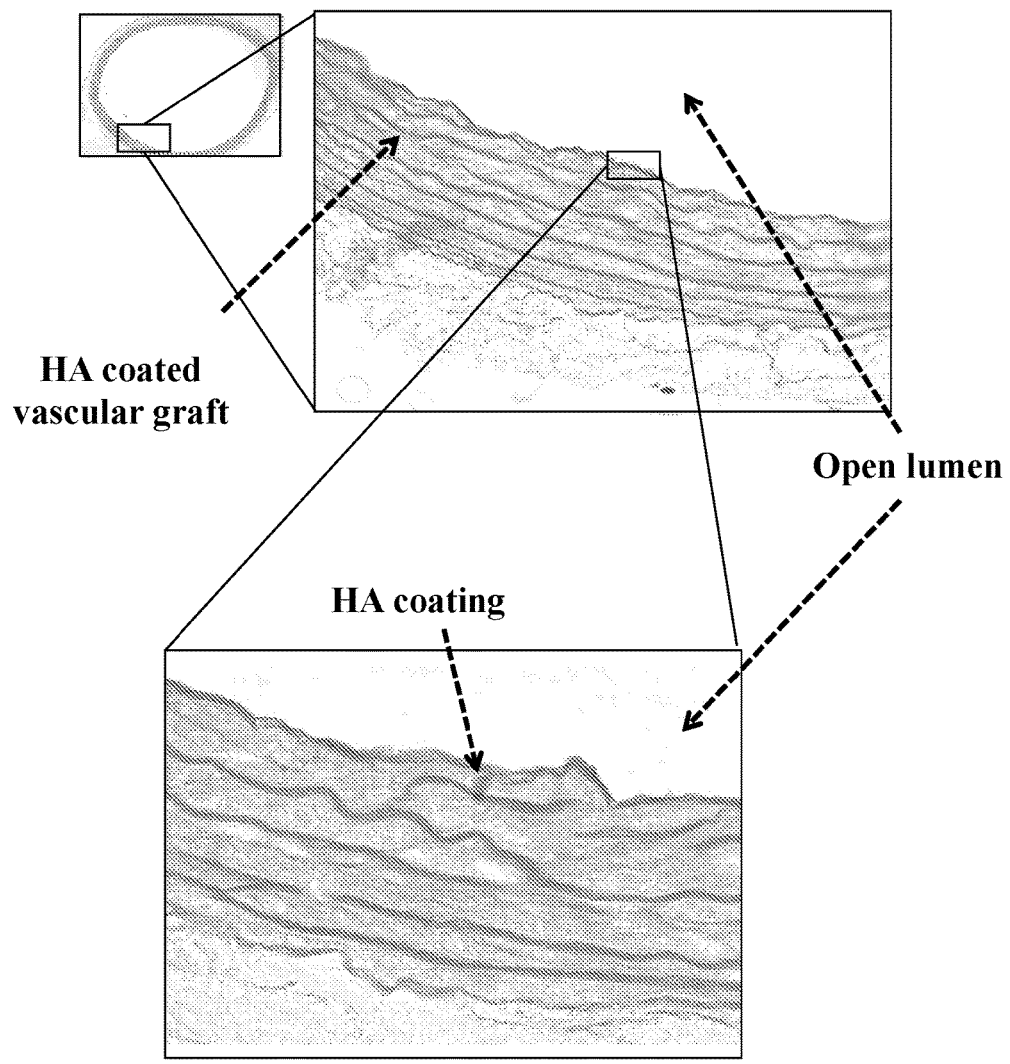
Figure 14, continued

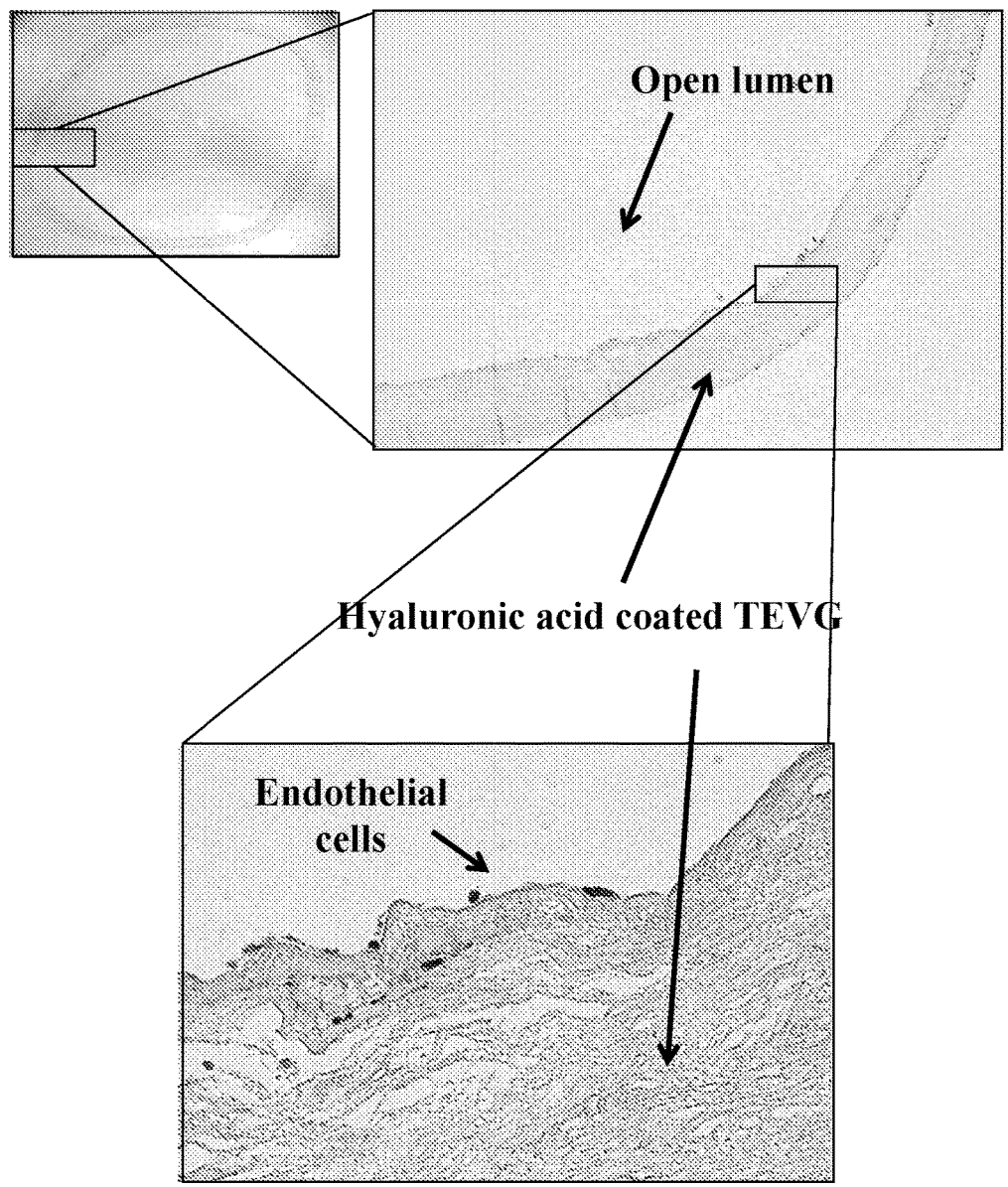
Figure 16, continued

ANTI-THROMBOGENIC GRAFTS

CROSS-REFERENCE TO RELATED APPLICATIONS

The present application is a 35 U.S.C. § 371 national phase application of, and claims priority to, International Application No. PCT/US2014/038597, filed May 19, 2014, and published under PCT Article 21(2) in English, which claims priority under 35 U.S.C. § 119(e) to U.S. Provisional Application No. 61/825,256, filed May 20, 2013, all of which applications are incorporated herein by reference in their entireties.

STATEMENT REGARDING FEDERALLY SPONSORED RESEARCH OR DEVELOPMENT

The invention was made with government support under HL083895 awarded by National Institute of Health. The government has certain rights in the invention.

BACKGROUND OF THE INVENTION

Vascular grafting is the use of transplanted blood vessels or synthetic scaffolds to replace, repair, or bypass damaged or potentially dangerous vessels. Vascular grafts are implanted into subjects with a wide variety of diseases and disorders, including cardiovascular disease, atherosclerosis, peripheral vascular disease, abdominal aortic aneurysm, and the like. These grafts can improve or restore blood flow to regions in which flow is obstructed. While autologous vessels or synthetic vessels made from biocompatible materials are traditionally used today, there has been some development in the use of decellularized structures as vascular grafts. Decellularized vascular grafts retain the shape and structure of native vessels, but are devoid of cells, thereby minimizing the immunogenicity of the grafts. Various decellularized biological structures are being developed as small-caliber vascular grafts. Currently their main drawback is high thrombogenicity, which can be reduced by recellularizing the luminal side of the implant with host cells. However, this solution implies at least a one month patient specific waiting time, due to required harvest and expansion of autologous endothelial cells to line the graft lumen. For clinical usage of newly emerging biological vascular grafts (such as tissue engineered and native decellularized grafts) a solution that will be available at the time of need is necessary for clinical application.

Thus, there is a need in the art for anti-thrombogenic coatings of vascular grafts. The present invention satisfies this unmet need.

SUMMARY OF THE INVENTION

As described below, the present invention includes anti-thrombogenic compositions, such as anti-thrombogenic vascular grafts, compositions comprising decellularized tissue coated with an anti-thrombogenic coating, methods of preparing anti-thrombogenic compositions, and methods of treatment comprising implanting the anti-thrombogenic compositions into a subject in need thereof.

One aspect of the invention includes a composition comprising a substrate having at least one surface coated with an anti-thrombogenic coating.

Another aspect includes a method of preparing a graft coated with an anti-thrombogenic coating, comprising the steps of: providing a substrate having at least one surface; and coating the at least one surface with an anti-thrombogenic coating, wherein said coating comprises: applying a first crosslinking solution to the surface; and applying a hydrogel solution to the surface, thereby providing a first layer on the surface of the substrate.

In another aspect, the invention includes a method of treating a diseased blood vessel in a subject, comprising bypassing the diseased blood vessel by implanting into the subject an anti-thrombogenic vascular graft, comprising a substrate having a luminal surface coated with an anti-thrombogenic coating.

In still another aspect, the invention includes a method of providing vascular access in a subject, comprising implanting into the subject an anti-thrombogenic vascular graft, comprising a substrate having a luminal surface coated with an anti-thrombogenic coating.

In various embodiments of the above aspects or any other aspect of the invention delineated herein, the anti-thrombogenic coating comprises a first layer comprising a hydrogel. In one embodiment, the first layer comprises hyaluronic acid, such as a thiol-modified hyaluronic acid. In another embodiment, the first layer is crosslinked to the at least one surface of the substrate, such as the luminal surface of the substrate. In yet another embodiment, the hydrogel solution comprises hyaluronic acid.

In another embodiment, the anti-thrombogenic coating further comprises a second layer comprising an anti-coagulant, wherein the second layer is crosslinked to the first layer. In some embodiments that include a second layer, the second layer comprises heparin. In another embodiment, the anti-coagulant solution comprises heparin.

In yet another embodiment, the substrate is a decellularized tissue, such as a decellularized blood vessel. In another embodiment, the decellularized tissue is a decellularized blood vessel having a luminal surface, and wherein the anti-thrombogenic coating is coated on the luminal surface of the decellularized blood vessel.

In still another embodiment, the coating further comprises applying a second crosslinking solution to the first layer and applying an anti-coagulant solution to the first layer, thereby providing a second layer atop the first layer.

In still yet another embodiment, the subject has a disorder selected from the group consisting of peripheral vascular disease, atherosclerosis, aneurysm, and venous thrombosis. In one embodiment, the subject is undergoing or is anticipated to undergo hemodialysis.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
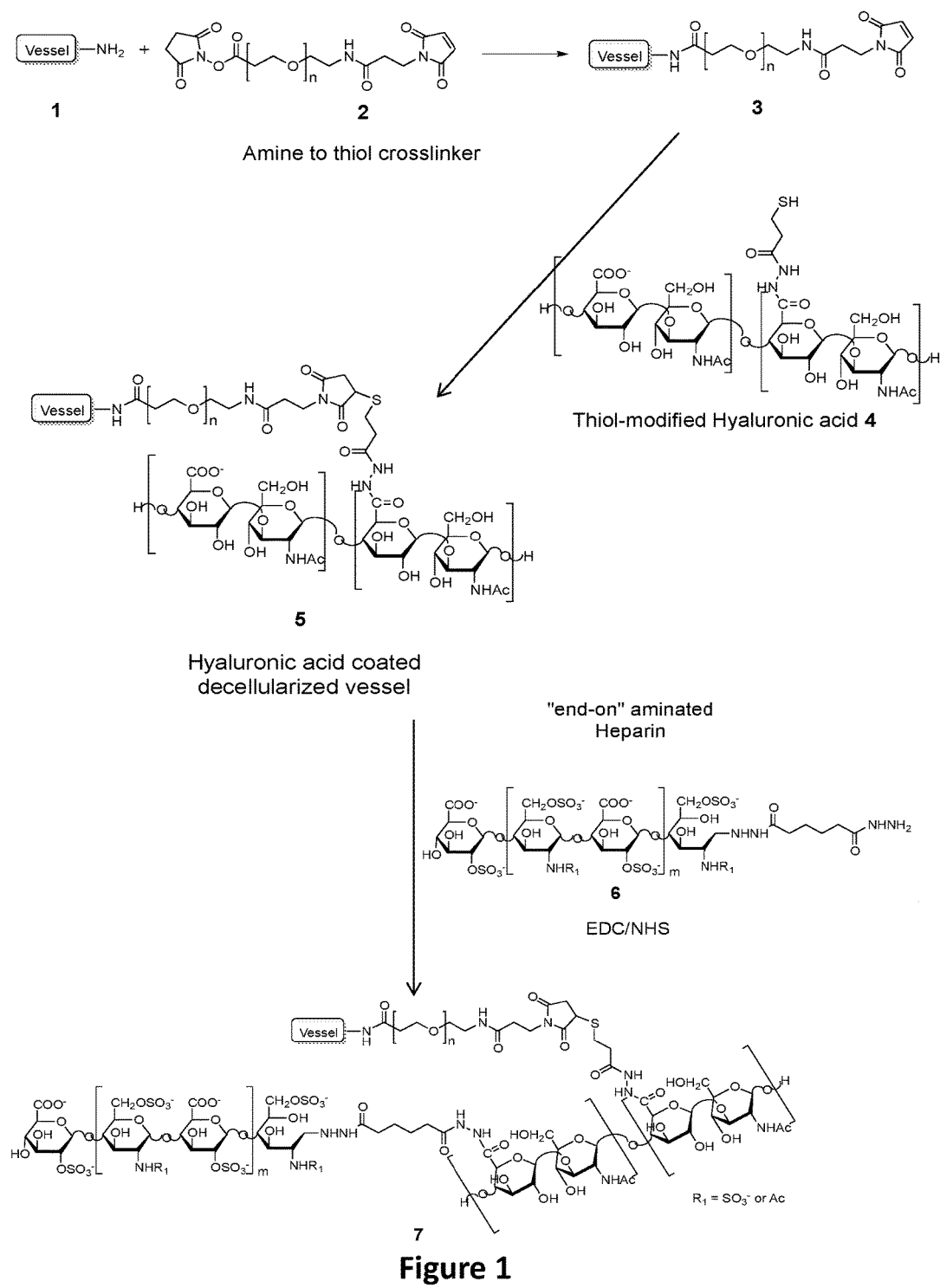
FIG. 1 is a schematic description of HA-heparin based coating of decellularized grafts structures, using thiolated-HA as a first layer of coating and "end-on" aminated heparin as a second layer of the coating.

The present invention relates to anti-thrombogenic coated compositions, methods of preparing such compositions, and methods of using such compositions. For example, in certain embodiments, the present invention provides vascular grafts coated with an anti-thrombogenic coating. The present invention is based upon the discovery that coating the luminal surface of a decellularized blood vessel with a layer of hyaluronic acid (HA) or a multilayer coating of HA and heparin or other molecules prevents thrombogenesis in the vessel. Thus, in one embodiment, the invention provides an anti-thrombogenic vascular graft composition comprising a decellularized blood vessel wherein the luminal surface of the blood vessel is coated with an HA layer. In another embodiment, the invention provides an anti-thrombogenic vascular graft composition comprising a decellularized blood vessel wherein the luminal surface of the blood vessel is coated with a multilayer coating where at least one layer comprises HA and at least one other layer comprises heparin. In one embodiment the HA layer is crosslinked to the luminal surface of the vessel. In one embodiment, the heparin layer is crosslinked to the HA layer. In certain embodiments, one or more layers of the coating comprise a hydrogel. In other embodiments, the HA layer is bound to other blood contacting surfaces, such as plastics contained in vascular grafts or catheters, or native vasculature that conducts blood.

The invention further provides methods of treatment comprising implanting an anti-thrombogenic composition of the invention to a recipient. For example, in one embodiment, the method comprises implanting a HA-coated or HA-heparin-coated vascular graft into a subject in need thereof. The coated vascular graft can be used, for example, to treat a subject having a diseased or blocked blood vessel. In certain embodiments, the coated vascular graft is used in a method of treating an aneurysm. In another embodiment, the coated vascular graft is used in a method of bypassing a diseased or blocked vessel. In another embodiment, the coated vascular graft is used in a method of providing vascular access in a subject undergoing or anticipated to undergo hemodialysis.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "abnormal," when used in the context of organisms, tissues, cells or components thereof, refers to those organisms, tissues, cells or components thereof that differ in at least one observable or detectable characteristic (e.g., age, treatment, or time of day) from those organisms, tissues, cells or components thereof that display the "normal" (expected) respective characteristic. Characteristics that are normal or expected for one cell or tissue type might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, to "alleviate" a disease, defect, disorder or condition means reducing the severity of one or more symptoms of the disease, defect, disorder or condition.

As used herein, "anti-coagulant" refers to an agent or class of agents that prevents coagulation or clotting of blood.

As used herein, "anti-thrombogenic coating" refers to a coating that reduces thrombus or blood clot formation.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the terms "biocompatible polymer" and "biocompatibility" when used in relation to polymers are recognized in the art. For example, biocompatible polymers include polymers that are generally neither toxic to the host, nor degrade (if the polymer degrades) at a rate that produces monomeric or oligomeric subunits or other byproducts at toxic concentrations in the host. In one embodiment, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in one embodiment, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

As used herein, "coating" refers to a covering that is applied to the surface of an object, usually a substrate. The coating may be continuous or non-continuous over the surface of the substrate. The coating may have one or more layers.

By "crosslinking" is meant creating a bond that links one polymer chain to another. Crosslinking may be induced through a crosslinking agent, solution or source or may be induced through self-assembly.

By "crosslinking agent" or "crosslinking source" is meant an agent that is capable of forming a chemical or ionic links between molecules. Non-limiting examples of crosslinking agents or sources include calcium chloride; ammonium persulfate (APS) and tetramethylethylenediamine (TEMED), glutaraldehyde, epoxides, oxidized dextran, p-azidobenzoyl hydrazide, N-[α-maleimiodoacetoxyl]succinimide ester, p-azidophenyl glyoxal monohydrate, bis-[β-(4-azidosalicylamido)ethyl]disulfide, bis[sulfosuccinimidyl] suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), riboflavin, heat, visible light irradiation, ultraviolet irradiation, blue light irradiation, and combinations thereof.

By "crosslinking solution" is meant a crosslinking agent in a solution or solvent.

The term "decellularized" or "decellularization" as used herein refers to a biostructure (e.g., an organ, or part of an organ, or a tissue), from which the cellular content has been removed leaving behind an intact acellular infra-structure. Some organs are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue cells, leaving behind the complex three-dimensional network of extracellular matrix. The connective tissue infra-structure is primarily composed of collagen. The decellularized structure provides a biocompatible substrate onto which different cell populations can be infused. Decellularized biostructures can be rigid, or semi-rigid, having an ability to alter their shapes.

The term "derived from" is used herein to mean to originate from a specified source.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is primarily water, the gel is referred to as a hydrogel.

As used herein, a "graft" refers to a composition that is implanted into an individual, typically to replace, correct or otherwise overcome a cell, tissue, or organ defect. A graft may comprise a scaffold. In certain embodiments, a graft comprises decellularized tissue. In some embodiments, the graft may comprise a cell, tissue, or organ. The graft may consist of cells or tissue that originate from the same individual; this graft is referred to herein by the following interchangeable terms: "autograft," "autologous transplant," "autologous implant" and "autologous graft." A graft comprising cells or tissue from a genetically different individual of the same species is referred to herein by the following interchangeable terms: "allograft," "allogeneic transplant," "allogeneic implant" and "allogeneic graft." A graft from an individual to his identical twin is referred to herein as an "isograft," a "syngeneic transplant," a "syngeneic implant" or a "syngeneic graft." A "xenograft," "xenogeneic transplant" or "xenogeneic implant" refers to a graft from one individual to another of a different species.

As used herein, the term "intact" refers to a state of being whereby an element is capable of performing its original function to a substantial extent.

"Photo-crosslinking" refers to bond formation that links one polymer chain to another upon exposure to light of appropriate wavelengths. For example, two polymers conjugated to a photoreactive group can be covalently photo-crosslinked by covalent bond formation between the photoreactive groups.

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combination thereof. A polymerization or cross-linking reaction may consume between about 0% and about 100% of the at least one functional group available in the system. In one embodiment, polymerization or cross-linking of at least one functional group results in about 100% consumption of the at least one functional group. In another embodiment, polymerization or cross-linking of at least one functional group results in less than about 100% consumption of the at least one functional group.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, "substrate" refers to a supporting material.

As used herein, "surface" refers to the outer most layer of a substrate or outermost part of the substrate.

As used herein, "thiol-modified" refers to one or more modifications to the substrate.

As used herein, to "treat" means reducing the frequency with which symptoms of a disease, defect, disorder, or adverse condition, and the like, are experienced by a patient.

The term "tissue," as used herein includes, but is not limited to, bone, neural tissue, fibrous connective tissue including tendons and ligaments, cartilage, dura, pericardia, muscle, lung, heart valves, veins and arteries and other vasculature, dermis, adipose tissue, or glandular tissue.

As used herein, "scaffold" refers to a structure, comprising a biocompatible material that provides a surface suitable for adherence of a substance. A scaffold may further provide mechanical stability and support. A scaffold may be in a particular shape or form so as to influence or delimit a three-dimensional shape or form. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, the term "treating a disease or disorder" means reducing the frequency with which a symptom of the disease or disorder is experienced by a patient. Disease and disorder are used interchangeably herein.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "effective amount" or "therapeutically effective amount" of a compound is that amount of compound that is sufficient to provide a beneficial effect to the subject to which the compound is administered.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions coated with an anti-thrombogenic coating, methods of making such compositions, and methods of using such compositions. In particular, the invention relates to biomaterials, tissue engineered constructs, and the like, which are coated with an anti-thrombogenic coating.

For example, in certain embodiments, the present invention provides vascular grafts coated with an anti-thrombogenic coating. However, the present invention is not limited to any particular type of material or construct. Rather, the present invention encompasses any material or construct coated with the anti-thrombogenic coating of the invention.

The present invention is based upon the discovery that coating the luminal surface of a decellularized blood vessel with a layer of hyaluronic acid (HA) or a multilayer coating of HA and heparin or other molecules prevents thrombogenesis in the vessel. Decellularized tissue has been investigated for use as vascular grafts. However untreated decellularized grafts are thrombogenic, unless they are recellularized with endothelial cells to inhibit clot formation, which is a time intensive process which can limit their clinical applicability. In one embodiment, the present invention is directed to a chemical coating, in lieu of cell seeding, to provide an anti-thrombogenic, anticoagulant graft. In certain embodiments, the coating is stable under standard refrigeration, thereby allowing for an off the shelf composition to be used as needed.

In one embodiment, the invention provides an anti-thrombogenic vascular graft composition comprising a decellularized blood vessel wherein the luminal surface of the blood vessel is coated with a first layer. In certain embodiments, the first layer comprises HA. In another embodiment, the invention provides an anti-thrombogenic vascular graft composition comprising a decellularized blood vessel wherein the luminal surface of the blood vessel is coated with a multilayer coating. In certain embodiments, the multilayer coating comprises a first layer comprising HA and a second layer comprising heparin. In one embodiment the HA layer is crosslinked to the luminal surface of the vessel. In one embodiment, the heparin layer is crosslinked to the HA layer. In certain embodiments, one or more layers of the coating comprise a hydrogel.

In one embodiment, the invention provides a method of making a composition coated with an anti-thrombogenic coating. In certain embodiments, the method comprises coating a surface of a substrate with a first layer. In one embodiment, the substrate is a decellularized tissue. However, the invention is not limited to any particular type of substrate. Rather, the method encompasses any suitable substrate known in the art, including, but not limited to, native blood vessels, engineered blood vessels, synthetic vascular grafts made from polymers, and blood-contacting catheters made from polymers. In one embodiment, the first layer comprises HA. In certain embodiments, the HA is thiol-modified HA. In certain embodiments, the method comprises using a crosslinker comprising N-hydroxysuccinimide ester (NHS) and maleimide to crosslink the amine groups of the substrate with the sulfhydryl groups of the HA. In certain embodiments, the method comprises a layer-by-layer coating procedure. In one embodiment, the method comprises coating the substrate with a second layer. In certain embodiments, the second layer is coated atop the first layer. For example, in one embodiment, the second layer comprises aminated heparin, which is crosslinked to the HA of the first layer.

The invention further provides methods of treatment comprising implanting an anti-thrombogenic composition of the invention. Such methods include implantation of one or more of a biomaterial, tissue engineering substrate, artificial organ, artificial tissue, artificial graft, and the like for treating a disease, disorder, or tissue defect in a subject in need thereof. For example, in one embodiment, the method comprises implanting a HA-coated or HA-heparin-coated vascular graft into a subject in need thereof. The coated vascular graft can be used, for example, to treat a subject having a diseased or blocked blood vessel. In certain embodiments, the coated vascular graft is used in a method of treating an aneurysm. In another embodiment, the coated vascular graft is used in a method of bypassing a diseased or blocked vessel. In another embodiment, the coated vascular graft is used in a method of providing vascular access in a subject undergoing or anticipated to undergo hemodialysis.

Composition

The present invention provides a composition comprising a surface coated with an anti-thrombogenic coating. In certain embodiments, the composition comprises a biomaterial, tissue engineering substrate, artificial organ, or artificial tissue having at least one surface coated with an anti-thrombogenic coating.

In one embodiment, the composition of the invention comprises a vascular graft having at least one surface coated with an anti-thrombogenic coating. In one embodiment, the vascular graft is a tubular vascular graft having an outer surface, an inner or luminal surface, and a hollow passageway. The tubular vascular grafts of the invention are biocompatible, properly proportioned as to appropriate dimensions such as diameter, length and wall thickness, readily attachable to the intended living tissue such as by sutures, and offer appropriate handling characteristics such as good flexibility, bending and resistance to kinking during bending. In certain embodiments, the tubular vascular graft of the invention is a conduit through which bodily fluids (e.g., blood) may flow through. The luminal surface of the tubular vascular graft therefore is the inner surface of the graft that, when implanted, is in contact with fluid. These tubular vascular grafts can thus be used to replace segments of native vessels, or otherwise can be used as artificial vessels serving to bypass native vessels. In another embodiment, tubular vascular grafts are used as vascular access points. In certain embodiments, the tubular vascular graft of the invention has mechanical properties substantially similar to native blood vessels. That is, the vascular grafts have the wall strength to withstand the pressure within the vessel. In one embodiment, the luminal surface of the tubular vascular graft is coated with a non-thromobogenic coating. The coating prevents platelet adhesion and thrombosis.

In certain embodiments, the tubular vascular graft of the invention has an inner diameter, outer diameter, length, and wall thickness as needed to mimic the native vessel being repaired, replaced, or bypassed. For example, in one embodiment, the tubular vascular graft of the invention is a small-caliber vascular graft, having an inner diameter of less than 5 cm.

In one embodiment, the tubular vascular graft of the invention as an inner diameter of about [1] mm to about [25] mm.

In one embodiment, the tubular vascular graft of the invention as an outer diameter of about [1] mm to about [25] mm.

In one embodiment, the tubular vascular graft of the invention has a wall thickness of about [100] µm to about [2] mm.

In one embodiment, the tubular vascular graft of the invention has a length of about [4] cm to about [100] cm.

In another embodiment, the vascular graft of the invention is a sheet graft. The sheet grafts of the invention can be used, for example, to patch portions of native blood vessels. As such, the sheet graft comprises a luminal surface that, when administered to the native vessel, is in contact with the fluid flowing through the vessel. In one embodiment, the luminal surface of the sheet graft is coated with a non-thromobogenic coating.

In certain embodiments, the composition of the invention comprises a substrate, where the surface comprises at least one surface coated with a non-thrombogenic coating. The substrate may be any material or biomaterial known in the art. For example, in certain embodiments, the substrate is an extracellular matrix protein composition, a collagen-based composition, an elastin-based composition, hydrogel, electrospun scaffold, injection molded polymeric scaffolds, woven and non-woven polymeric scaffolds, metal-based implants, ceramic composite biomaterials, or other tissue engineering substrate.

In one embodiment, the substrate is decellularized tissue. Decellularized tissue substrates are substrates obtained from harvesting tissue from a donor source and removing cells and cellular debris from the harvested tissue. The decellularized tissue substrates retain the structure of the harvested tissue and can subsequently be used as tissue engineering substrates to be implanted into a subject in need. Methods of producing decellularized tissue substrates are well known in the art. The present invention is not limited to any particular type of decellularized tissue or the manner at which the decellularized tissue was produced.

In certain embodiments, decellularization relies on a chemical methodology. In some instances, decellularization comprises a chemical methodology combined with mechanical means in order to remove cells from the tissue. In one aspect, the chemical solution or otherwise referred to as the decellularization solution used for decellularization generally includes at least a hypertonic solution, a detergent, and a chelating agent. In certain embodiments, the hypertonic solution is a hypertonic sodium chloride solution. In certain embodiments, the detergent is a zwitterionic detergent such as CHAPS. In certain embodiments, the chelating agent is EDTA.

In one embodiment, the decellularization solution can include a buffer (e.g., PBS) for osmotic compatibility with the cells. In some instances, the decellularization solution also can include enzymes such as, without limitation, one or more collagenases, one or more dispases, one or more DNases, or a protease such as trypsin. In some instances, the decellularization solution also or alternatively can include inhibitors of one or more enzymes (e.g., protease inhibitors, nuclease inhibitors, and/or collegenase inhibitors).

In certain instances, a method of producing a decellularized tissue substrate includes perfusing the tissue with the decellularization solution. The pressure for which the decellularization solution is perfused through the tissue can be adjusted to the desired pressure. In one embodiment, the decellularization solution is perfused through the tissue at perfusion pressure below about 30 mmHg. In one embodiment, the decellularization solution is perfused through the tissue at pressures less than about 20 mmHg.

In certain embodiments, the decellularized tissue substrate is a decellularized blood vessel. For example, a decellularized blood vessel can serve as a substrate for tubular vascular grafts described elsewhere herein. In one embodiment, the decellularization solution can be introduced into blood vessel to effect cell removal. In certain embodiments, decellularization of blood vessels removes the native endothelium lining of the vessel.

In one embodiment, the decellularized tissue of the invention consists essentially of the extracellular matrix (ECM) component of all or most regions of the tissue. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, epithelial cells, and nuclei in histologic sections using standard histological staining procedures. Preferably, but not necessarily, residual cell debris also has been removed from the decellularized tissue.

In one embodiment, the decellularization process of a natural tissue preserves the native 3-dimensional structure of the tissue. That is, the morphology and the architecture of the tissue, including ECM components are maintained during and following the process of decellularization. The morphology and architecture of the ECM can be examined visually and/or histologically. For example, the basal lamina on the exterior surface of a solid organ or within the vasculature of an organ or tissue should not be removed or significantly damaged due to decellularization. In addition, the fibrils of the ECM should be similar to or significantly unchanged from that of an organ or tissue that has not been decellularized.

In one embodiment, one or more compounds can be applied in or on a decellularized tissue to, for example, preserve the decellularized tissue, or to prepare the decellularized tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue can be further treated with, for example, irradiation (e.g., UV, gamma) to reduce or eliminate the presence of any type of microorganism remaining on or in a decellularized tissue.

Exemplary decellularization methods are used to generate a decellularized tissue provides a controlled, precise way to destroy cells of a tissue, while leaving the underlying ECM, including vascularization, and other gross morphological features of the original tissue intact. In certain embodiments, the decellularized substrates are then suitable for seeding with appropriate cells. In one embodiment, the decellularized substrates are not seeded with cells. In certain embodiments, the decellularized substrates are coated with a non-thrombogenic coating described elsewhere herein. Where the process is performed in vitro, the decellularized tissue is suitable for implantation into the recipient as a replacement tissue. The present invention includes methods of fabrication of engineered tissues built from such substrates.

Although the source of the tissue is not limited, in exemplary embodiments, the tissue is from a relatively large animal or an animal recognized as having a similar anatomy (with regard to the tissue of interest) as a human, such as a pig, a cow, a horse, a monkey, or an ape. In some embodiments, the source of the tissue is human, use of which can reduce the possibility of rejection of engineered tissues based on the scaffold. In certain embodiments, the tissue is engineered in vitro from cells, and then subjected to decellularization. In certain embodiments, the tissue is a blood vessel obtained from the animal. Any suitable blood vessel may be used to produce the decellularized blood vessel substrate. For example, in one embodiment, the decellularized substrate produced from the aorta, or portion thereof, obtained from the donor animal or from coronary artery, saphenous vein, posterior tibial artery, pulmonary artery, external iliac artery, right inferior mammary artery, radial artery.

The composition of the invention comprises at least one surface coated with a non-thrombogenic coating. In certain embodiments, the non-thrombogenic coating prevents platelet adhesion and activation, thereby reducing thrombosis. For example, in certain embodiments, the coating prevents access of collagen, or other thrombogenic components that may be present in the substrate, to the blood stream. In one embodiment, the coating of the invention is a single layer coating. In another embodiment, the coating of the invention is a multi-layer coating. In one embodiment, the coating comprises a hydrogel layer. For example, in certain embodiments, the composition comprises a first layer comprising a hydrogel crosslinked to the substrate. The first layer is sometimes referred to herein as the hydrogel layer. In one embodiment, the hydrogel layer comprises thiol-modified hyaluronic acid (HA) or dihydrazide-modified HA or unmodified HA.

The hydrogel may comprise any biopolymer or synthetic polymer known in the art. For example, the hydrogel may comprise hyaluronans, chitosans, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12).

Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12). In some embodiments, the transparent hydrogel scaffold comprises poly(ethylene glycol) diacrylate (PEGDA).

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels can also be made degradable in vivo by incorporating PLA, PLGA or PGA polymers. Moreover, hydrogels can be modified with fibronectin, laminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23(22):4307-14; Ifkovits and Burkick, 2007, Tissue Eng. 13(10):2369-85).

In certain embodiments, the hydrogel of the invention is crosslinked Crosslinking of the hydrogel may be performed using any suitable method known in the art. In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art. In certain embodiments, the hydrogel comprises a photo-activated crosslinking agent. In one embodiment, one or more components of the hydrogel is cross-linked upon exposure to UV light.

In certain embodiments, the hydrogel is crosslinked using a heterobifunctional crosslinker comprising NHS and maleimide. In a particular embodiment, the crosslinker links the hydrogel layer directly to the substrate. For example, in one embodiment, the NHS reacts with the amine groups on the decellularized vessel substrate, while the malemide reacts with the sulfhydryl groups on the thiol-modified HA (FIG. 1). In certain embodiments the hydrogel is crosslinked using a homobifunctional crosslinker comprising imidoester reactive groups such as the DMA (Dimethyl adipimidate.2 HCl) crosslinker, which is reactive towards amine groups. In a particular embodiment, the crosslinker links the hydrogel layer directly to the substrate. For example, in one embodiment, the imidoester reacts with the amine groups on the decellularized vessel substrate, and the amine groups on the dihydrazide-Modified HA.

In certain embodiments the hydrogel is crosslinked using EDC/NHS crosslinker which crosslinks carboxyl and amine groups. In a particular embodiment, the crosslinker links the hydrogel layer directly to the substrate. For example, in one embodiment, the EDC/NHS reacts with the carboxyl groups of the unmodified HA and the amine groups on the decellularized vessel substrate.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art.

In another embodiment utilizing a cross-linking agent, polyacrylated materials, such as ethoxylated (20) trimethylpropane triacrylate, may be used as a non-specific photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine Continuous exposure of this reactive mixture to long-wavelength light (>498 nm) would produce a cross-linked hydrogel network The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. In addition the gels can be loaded with growth factors: basic fibroblast growth factor (bFGF) and/or vascular endothelial growth factor (VEGF), VEGF or bFGF is incorporated to the hyaluronic acid gel prior to the addition of the crosslinker. Crosslinking then proceeds with no other modifications entrapping the growth factors within the hyaluronic acid gels. This promotes re-endothelialization of the gels by the neighboring endothelial cells of the implantation site. The growth factors may be added at a concentration of 50 ng/cm$^2$ area of vessel to be cross-linked. The enhancing agents can also be added to the matrix composition during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

In one embodiment, the hydrogel layer may comprise one or more therapeutic agents. For example, one or more therapeutic agents can be embedded within the hydrogel layer. In another embodiment, the hydrogel layer can be modified with functional groups for covalently attaching a variety of proteins (e.g., collagen) or compounds such as therapeutic agents. Therapeutic agents include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents, or peptide/protein growth factors or cytokines. It is contemplated that linkage of the therapeutic agent to the matrix can be via a protease sensitive linker or other biodegradable linkage. Molecules which can be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In certain embodiments, the hydrogel layer, coated along the luminal surface of the substrate, has a thickness of about [100] nm to about [3] mm. In certain embodiments, the hydrogel layer is coated with a second layer. For example, in one embodiment, the hydrogel layer is coated with a second layer comprising an anti-coagulant. For example, in one embodiment, the second layer comprises heparin or derivatives thereof. However, the present invention is not limited to the use of heparin as an anti-coagulant. Rather, any known anti-coagulant may be used. Exemplary anti-coagulants include, but are not limited to vitamin K antagonists, coumarins, Curcumin (diferuloyl methane), Hirudin, heparins, Factor Xa inhibitors, direct Xa inhibitors, direct thrombin inhibitors, natural polysaccharides and synthetic ones based on β-(1-4)linked anhydroglucose units, chondroitin sulfate, glycosaminoglycans, and the like.

Figure 2A:
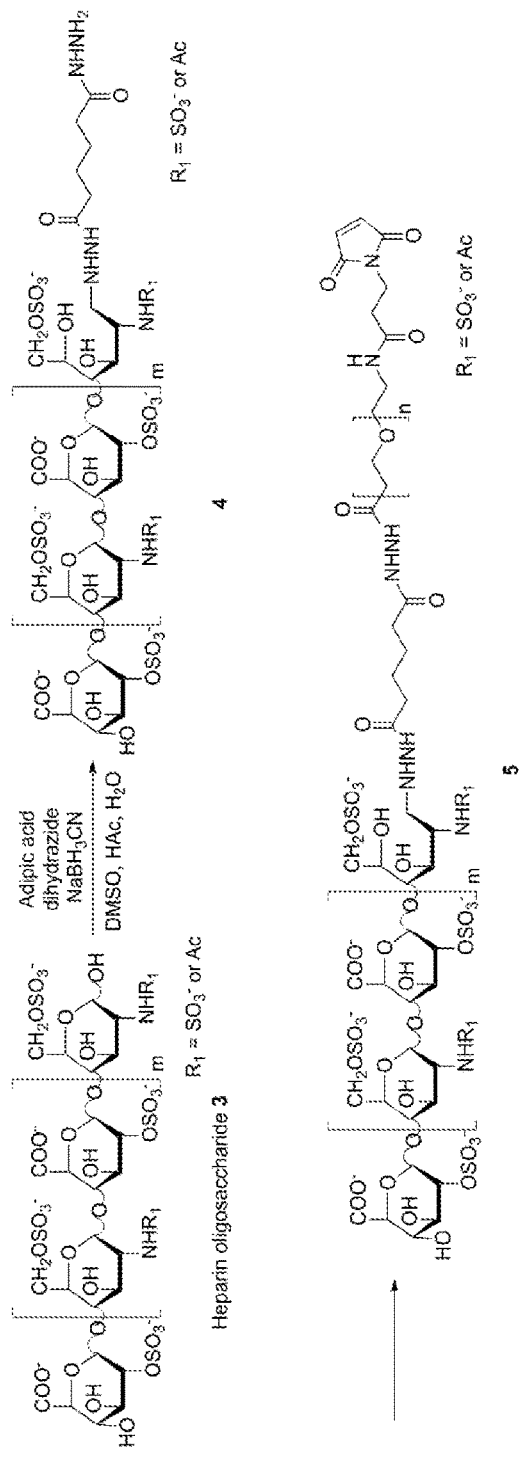
FIG. 2A depicts the schematic description of heparin modification for "end-on" heparin modification and Sulfo-SMCC addition for spontaneous heparin crosslinking onto hyaluronic acid coated decellularized vessels.
Figure 2B:
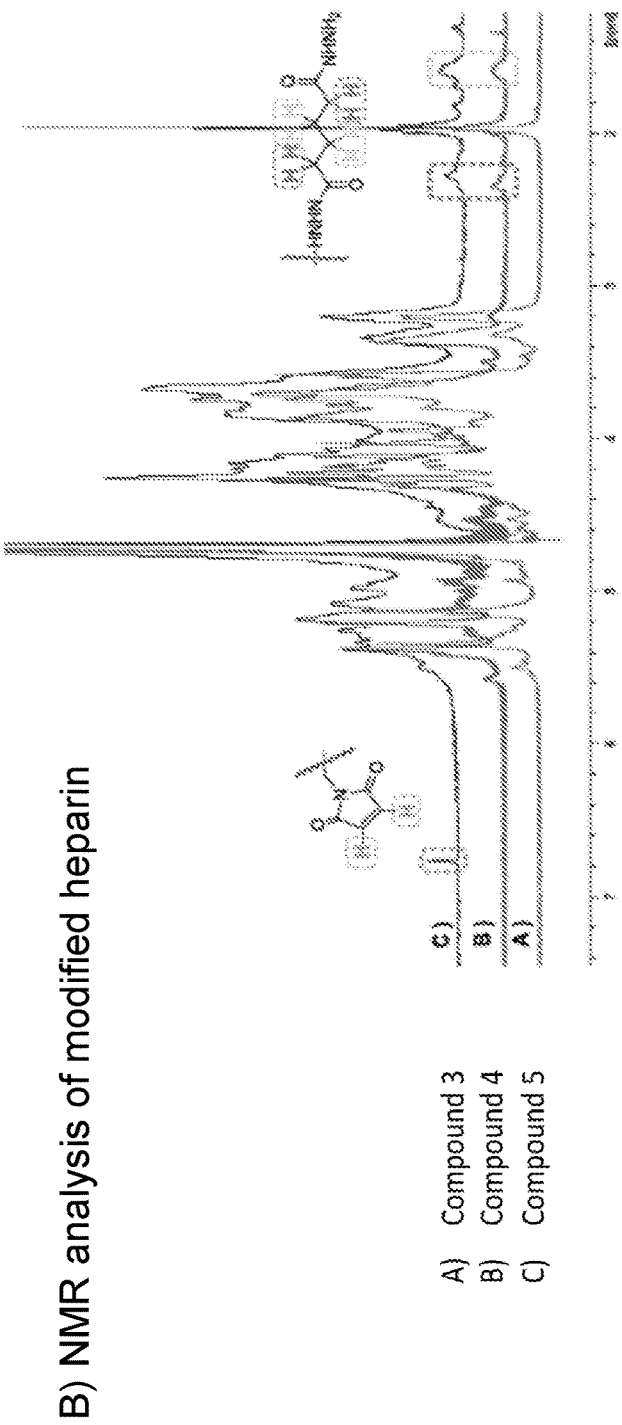
FIG. 2B depicts the NMR characterization of heparin modification.
Figure 3:
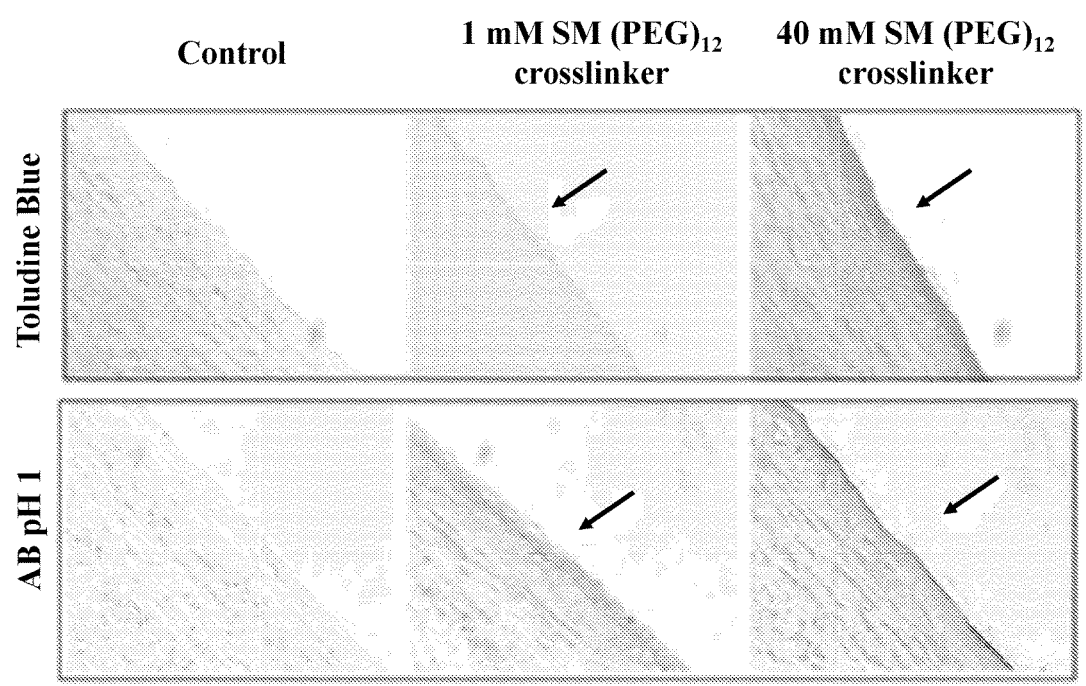
FIG. 3 is a set of images depicting the cross-sections of HA coated decellularized porcine abdominal aortas using increasing concentrations of SM(PEG)$_{12}$ crosslinker (NHS-maleimide crosslinker). As the concentration of the cross-linker increases, so does the coating smoothness and thickness as demonstrated by the increasing thick layer of blue dye on the surface (Toluidine Blue), and orange dye layer (Alamar Blue pH 1). The coating is indicated by arrows in both Toluidine Blue and Alamar Blue pH 1 (AB pH 1).

In one embodiment, the second layer is crosslinked to the first layer. For example, in one embodiment, the anti-coagulant of the second layer is crosslinked to the hyaluronic acid of the first layer (e.g., hydrogel layer). In one embodiment, the anti-coagulant of the second layer is modified, which in certain instances allows for easier crosslinking to the first layer. For example, in certain embodiments, the second layer comprises aminated heparin, wherein the heparin comprises a primary amine group. In one embodiment, the heparin is aminated at the end-chain electrophilic carbon atom ("end-on amination") (FIG. 2).

In certain embodiments, the aminated heparin is crosslinked to the hyaluronic acid via EDC/NHS. However, the composition of the invention is not limited to any particular crosslinker Rather any type or crosslinker known in the art that is suitable to crosslink one or more components of the first layer to one or more components of the second layer may be used. In one embodiment, the aminated heparin of the second layer is crosslinked to the carboxyl groups of the HA of the first layer. In another embodiment, the aminated heparin is crosslinked to thiol groups of the HA of the first layer. For example, in certain embodiments, the aminated heparin is further modified to contain NHS and a sulfhydryl-reactive malemide group. This modified heparin can then spontaneously react with the remaining thiol groups of the thiol-modified HA of the first layer (FIG. 2).

In one embodiment, the heparin of the second layer extends luminally, thereby exposing the active pentasaccharide sequence of heparin to the blood stream when the composition is implanted. This conformation thereby prevents immediate activation of coagulation.

The coating of the anti-thrombogenic compositions of the invention is biocompatible and non-toxic. For example, it is demonstrated elsewhere herein that cells contacted to the coating can survive and proliferate. Thus, while in certain embodiments, the compositions of the invention are not recellularized prior to implantation in a subject, the compositions are conducive to in vivo recellularization of native cells. In certain embodiments, the in vivo recellularization degrades the coating over time.

In certain embodiment, the coating of the anti-thrombogenic compositions of the invention is non-immunogenic. That is, the coating does not induce an immune response in the subject.

Methods of Preparing

The present invention provides a method of making compositions having at least one surface coated with a non-thrombogenic coating. As discussed elsewhere herein, the composition of the invention comprises a substrate, for example a biomaterial, tissue engineering substrate, or the like, wherein at least one surface of the substrate is coated with a non-thrombogenic coating. In certain embodiments, the substrate comprises decellularized tissue. As discussed elsewhere herein, the present invention is not limited to any particular decellularized tissue, nor is it limited to any particular method of generating decellularized tissue. Exemplary methods of producing decellularized tissue are discussed elsewhere herein and are well known in the art, see for example US2012/0064050 and WO2007/025233, each of which are herein incorporated by reference in their entireties.

The method comprises coating a surface of the substrate with the non-thrombogenic coating. As discussed elsewhere herein, the coating, in certain embodiments comprises a single layer or a multi-layer coating. In one embodiment, the method comprises perfusing the substrate with one or more solutions. In certain embodiments, the decellularized tissue substrate is perfused with water, saline, or the like, prior to application of the non-thromobogenic coating.

As discussed elsewhere herein, in certain embodiments, the composition of the invention comprises a hydrogel layer crosslinked to a decellularized tissue substrate. In one embodiment, the decellularized tissue substrate is perfused with a crosslinking containing solution. The present invention is not limited to any particular type of crosslinker. Rather, any suitable crosslinker known in the art may be employed. In one embodiment, the crosslinker is SM(PEG)n NHS-PEG-Malemide crosslinker (Thermo). In one embodiment, the crosslinker is dissolved in DMSO and PBS to form a crosslinking solution. The relative amount of the crosslinker in the crosslinking solution may be varied as appropriate. In certain embodiments, the concentration of the crosslinker in the crosslinking solution is about 0.1 mM to about 500 mM. In another embodiment, the concentration of the crosslinker in the crosslinking solution is about 1 mM to about 100 mM. In another embodiment, the concentration of the crosslinker in the crosslinking solution is about 40 mM. The crosslinker solution may be then perfused onto the decellularized tissue substrate. As discussed elsewhere herein, in certain embodiments the substrate is a decellularized blood vessel. In one embodiment, the tubular decellularized vessel is continuously perfused with the solution through the lumen of the vessel. In one embodiment, the solution is perfused in a closed loop fashion. In one embodiment, the substrate is perfused with the crosslinking solution for about 5 seconds to about 2 hours. In another embodiment, the substrate is perfused with the crosslinking solution for about 30 seconds to about 24 hours. In another embodiment, the substrate is perfused with the crosslinking solution for about 30 minutes.

In certain embodiments, after application of the crosslinking solution, the substrate is perfused with a hydrogel solution. As discussed elsewhere herein, the hydrogel solution may comprise any suitable biopolymer, synthetic polymer, or combination thereof. In one embodiment, the hydrogel solution comprises HA. In one embodiment, the hydrogel solution comprises thiol-modified HA. The hydrogel solution may be produced by dissolving the thiol-modified HA into water or other suitable solvent. In certain embodiments, the solvent is degassed, as in certain instances, the HA will crosslink in the presence of oxygen. In one embodiment, the tubular decellularized vessel is continuously perfused with the hydrogel solution through the lumen of the vessel. In one embodiment, the solution is perfused in a closed loop fashion. In one embodiment, the substrate is perfused with the hydrogel solution for about 5 seconds to about 8 hours. In another embodiment, the substrate is perfused with the hydrogel solution for about 30 seconds to about 4 hours. In another embodiment, the substrate is perfused with the crosslinking solution for about 2 hours. After perfusion of the hydrogel solution, in certain embodiments, the substrate is rinsed with water, saline, or the like. In certain embodiments, in order to produce a rough morphology of the luminal surface, the substrate is perfused with a solution comprising hylaronidase and collagenase.

In one embodiment, the substrate is coated with a second layer comprising an anti-coagulant. For example, in one embodiment, the second layer comprises heparin or derivatives thereof. However, the present invention is not limited to the use of heparin as an anti-coagulant. Rather, any known anti-coagulant may be used. Exemplary anti-coagulants include, but are not limited to vitamin K antagonists, coumarins, curcumin (diferuloyl methane), hirudin, heparins, Factor Xa inhibitors, direct Xa inhibitors, direct thrombin inhibitors, natural polysaccharides and synthetic ones based on $\beta$-(1→4)-linked anhydroglucose units and the like. As discussed elsewhere herein, in certain embodiments, the heparin is modified. In one embodiment, ADH-amino modified heparin is prepared by dissolving heparin into a suitable solvent, for example, formamide, and adding adipic acid dihyrazide (ADH). In one embodiment, aqueous sodium cyanoborohydride is added to the mixture. In some embodiments, the mixture is then dialyzed. The retentate may then be lyophilized and purified, for example, by ethanol precipitation.

In certain embodiments, coating of the substrate with the second layer comprises first perfusing the substrate with a second crosslinking solution. For example, in one embodiment, the method comprises perfusing a second crosslinking solution comprising EDC and NHS. In one embodiment, the second crosslinking solution comprises water, saline, or other suitable buffer. For example, in certain embodiments the second crosslinking solution comprises NaCl/MES buffer. In certain embodiments, the EDC/NHS of the second crosslinking solution allows for crosslinking of the second layer to the carboxyl groups of the HA of the first layer. In one embodiment, the substrate is perfused with the second crosslinking solution for about 5 seconds to about 2 hours. In another embodiment, the substrate is perfused with the second crosslinking solution for about 30 seconds to about 1 hour. In another embodiment, the substrate is perfused with the second crosslinking solution for about 15 minutes.

In certain embodiments, coating of the substrate with the second layer comprises first activating with a crosslinking solution the heparin (or any known anti-coagulant) before perfusion on the substrate. For example in one embodiment the method comprises the addition of hetero-bifunctional crosslinkers such as Sulfo-SMCC activating the aminated heparin. This allows the pre-activated amine groups of heparin to crosslink spontaniously on accessible thiol groups on the first layer. In a second embodiment the heparin (or any known anti-coagulant) carboxyl groups are activated via a crosslinking solution comprising EDC and NHS. The substrate is perfused with the second crosslinking solution for about 5 seconds to about 2 hours. In another embodiment, the substrate is perfused with the second crosslinking solution for about 30 seconds to about 1 hour. In another embodiment, the substrate is perfused with the second crosslinking solution for about 15 minutes.

In certain embodiments, coating of the substrate with the second layer comprises perfusing the substrate with an anti-coagulant solution. For example, in certain embodiments, the anti-coagulant solution comprises a heparin solution. The heparin solution comprises heparin dissolved in a suitable solvent, including, but not limited to, water, saline, or other buffer. For example, in one embodiment, heparin is dissolved in NaCl/MES buffer. As described elsewhere herein, in certain embodiments, the heparin of the heparin solution is modified. The amount of heparin in the heparin solution may be varied as necessary. For example, the amount of heparin may, in certain instances, depend on the ultimate use of the composition. In certain embodiments, the concentration of heparin in the heparin solution is [5 $\mu$M]. In one embodiment, the substrate is perfused with the heparin solution for about 5 seconds to about 3 hours. In another embodiment, the substrate is perfused with the heparin solution for about 30 seconds to about 2 hours. In another embodiment, the substrate is perfused with the second crosslinking solution for about 1 hour. In certain embodiments, the substrate is rinsed with water, saline, or other suitable buffer following perfusion of the heparin solution.

Although an advantage of the present invention is that recellularization is not required, a skilled artisan armed with the specification would recognize that the decelluarized tissue can be recellularized if desired. Accordingly, in certain embodiments, the method comprises ex vivo or in vitro culturing of cells on the surface of the substrate, or on the coating of the substrate. The cultured cells can be induced to proliferate throughout at least a portion of the composition. For example, in certain embodiments, cells are cultured such that they produce a confluent layer of cells on the luminal surface of a vascular graft composition described herein. The cells can also differentiate in vitro by culturing the cells in differentiation. Alternatively, the cells can differentiate in vivo when they establish contact with a tissue within the mammal or when the cells are sufficiently close to a tissue to be influenced by substances (e.g., growth factors, enzymes, or hormones) released from the tissue.

As described elsewhere herein, in certain embodiments, the substrate of the composition is decellularized tissue. Therefore, in certain embodiments, the method comprises recellularization of the substrate.

The number of cells that is introduced into and onto a decellularized organ in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be seeded with at least about 1,000 (e.g., at least 10,000, 100,000, 1,000,000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

Cells can be introduced to a decellularized organ or tissue by injection into one or more locations. In addition, more than one type of cell (i.e., a cocktail of cells) can be introduced into a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a cannulated decellularized organ or tissue. For example, cells can be perfused into a decellularized organ using a perfusion medium, which can then be changed to an expansion and/or differentiation medium to induce growth and/or differentiation of the regenerative cells. In the case of a lung tissue, the cells can be introduced into either or both of the airway compartment via the trachea, or the vascular compartment via the pulmonary artery or vein.

During recellularization, an organ or tissue is maintained under conditions in which at least some of the regenerative cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the cells attached thereto are maintained in a suitable environment. For example, the cells may require a nutritional supplement (e.g., nutrients and/or a carbon source such as glucose), exogenous hormones or growth factors, and/or a particular pH.

Cells can be allogeneic to a decellularized organ or tissue (e.g., a human decellularized organ or tissue seeded with human cells), or regenerative cells can be xenogeneic to a decellularized organ or tissue (e.g., a pig decellularized organ or tissue seeded with human cells).

In some instances, an organ or tissue generated by the methods described herein is to be transplanted into a patient. In those cases, the cells used to recellularize a decellularized organ or tissue can be obtained from the patient such that the regenerative cells are autologous to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue can be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

In certain instances, a decellularized tissue may be recellularized with cells in vivo (e.g., after the tissue has been transplanted into an individual). In vivo recellularization may be performed as described above (e.g., injection and/or perfusion) with, for example, any of the cells described herein. Alternatively or additionally, in vivo seeding of a decellularized organ or tissue with endogenous cells may occur naturally or be mediated by factors delivered to the recellularized tissue.

Methods of Use

The present invention provides therapeutic methods comprising the administration or implantation of the anti-thrombogenic compositions (e.g., anti-thrombogenic vascular grafts) described herein. For example, in certain embodiments, the anti-thrombogenic vascular grafts of the invention are used in methods to replace or bypass damaged or diseased blood vessels in a subject. In certain embodiments, the methods are used to treat an aneurysm in a subject. In another embodiment, the methods are used to replace or bypass vessels which provide inadequate blood flow.

In certain embodiments, the method comprises treating a subject having a diseased blood vessel. For example, exemplary diseases or disorders treated by way of the present method include, but are not limited to, peripheral vascular disease, atherosclerosis, aneurysm, or venous thrombosis. In one embodiment, the subject is a mammal. In one embodiment, the subject is a human.

Grafting of the substrates and compositions of the invention to an organ or tissue to be augmented can be performed according to the methods described in herein or according to art-recognized methods. The composition can be grafted to an organ or tissue of the subject by suturing the graft material to the target organ. Implanting a neo-organ construct for total organ replacement can be performed according to the methods described herein or according to art-recognized surgical methods.

In certain embodiments vascular grafts of the invention are sutured to existing blood vessels of the subject. For example, an anti-thrombogenic vascular graft described herein may be sized and shaped appropriately to mimic or replace a particular damaged or abnormal blood vessel of the subject. In certain embodiments, the region of native blood vessel to be replaced is surgically excised from the subject. The ends of the vascular graft of the invention can then be sutured to the remaining vessel.

The vascular grafts of this invention may be used in place of any current by-pass or shunting graft, either natural or artificial, in any application. Thus, they may be used for, without limitation, arterial by-pass, both of the cardiac variety and that used to treat peripheral vascular disease (PVD). A graft of this invention may also be used as a replacement or substitute for a fistula created for use in hemodialysis. Also the vascular graft of the present invention can be used to replace a damaged blood vessel such as traumatically damaged limb arteries.

In certain embodiments, the method of the invention comprises implantation of the graft of the invention to provide an artificial arteriovenous shunt or graft for use by dialysis patients. In hemodyalysis, a patient's blood is "cleansed" by passing it through a dialyzer, which consists of two chambers separated by a thin membrane. Blood passes through the chamber on one side of the membrane and dialysis fluid circulates on the other. Waste materials in the blood pass through the membrane into the dialysis fluid, which is discarded, and the "clean" blood is re-circulated into the blood stream. Access to the bloodstream can be external or internal. External access involves two catheters, one placed in an artery and one in a vein. More frequently, and preferably, internal access is provided. This is accomplished either by an artriovenous fistula or an AV graft. An AV fistula involves the surgical joining of an artery and a vein under the skin. The increased blood volume stretches the elastic vein to allow for a larger volume of blood flow. Needles are placed in the fistula so that blood can be withdrawn for dialysis and then the blood is returned through the dilated vein.

An AV graft may be used for people whose veins, for one reason or another, are unsuitable for an AV fistula. An AV graft involves surgically grafting a donor vein from the patient's own saphenous vein, a carotid artery from a cow or a synthetic graft from an artery to a vein of the patient. One of the major complications with a synthetic AV graft is thrombosis and neointimal cell proliferation that cause closure of the graft.

As described elsewhere herein, a benefit of the vascular grafts of the invention are that they are non-thrombogenic without the need seeding of the graft with the subject or donor cells. As such, the grafts can be implanted at the time that it becomes necessary. That is, there is no waiting time needed in order to prepare the grafts. The grafts of the invention are stable during standard refrigeration, and thus can serve as an off the shelf composition.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Hyaluronic Acid-Heparin Based Coatings for Biological Substrates

Described herein is the development of a coating for decellularized biological structures (native and tissue engineered) built from a first layer of thiol-modified hyaluronic acid (HA; also known as hyaluronan) and a second layer of modified heparin.

HA Coating

Thiol-modified HA (Glycosan, San Francisco, USA) was crosslinked onto decellularized biological structures amines groups ($NH_2$) using the sulfhydryl (SH) groups on the HA. This was accomplished via heterobifunctional crosslinker made up of N-hydroxysuccinimide ester (NHS) and maleimide where NHS reacts with the amine groups on the decellularized vessels and maleimide reacted with the sulfhydryl groups on the hyaluronic acid. The crosslinked hyaluronic acid created a few microns thick continuous layer over the length of the tubular vessel, "hiding" the exposed collagen of decellularized vessels.

Heparin Modification and Modified Heparin Coating

The second step of the coating was the "end on" aminated heparin, produced via reductive amination, which was crosslinked onto the carboxyl (COOH) groups of the hyaluronic acid via EDC/NHS. The "end-on" heparin amination was accomplished on the heparin end-chain electrophilic carbon atom, which under heat attacked the nucleophilic nitrogen of adipic acid dihydrazide (ADH) primary amine to yield a weak bond stabilized using sodium cyanoborohydride ($NaCNBH_3$). This yielded an end-on primary amine group on the heparin (FIG. 2A Top). The end-on aminated heparin was cleaned via dialysis, and crosslinked onto the remaining carboxyl (COOH) groups of the HA coating via EDC/NHS. Heparin attached in this manner extended luminally (due to hydration) exposing the active pentasaccharide sequence of heparin preventing immediate activation of coagulation. This reaction was schematically described in FIG. 1.

In certain instances, heparin modification comprises an additional step. The heparin modification can be taken further by modifying the ADH primary amine with Sulfosuccinimidyl-4-(N-maleimidomethyl)cyclohexane-1-carboxylate (Sulfo-SMCC) (FIG. 2A Bottom). This route used the ADH-amine to link NHS leaving a sulfhydryl-reactive maleimide group. The modified heparin was spontaneously reactive with the remaining thiol groups on the hyaluronic coatings.

Rat Aorta Isolation

Sprague Dawley rats ascending aorta was harvested under general anesthesia (isoflorane). Briefly, the rats were opened by a midline laparotomy and the ascending aorta was dissected free. The aorta was then rinsed with cold PBS and was subjected to decellularization within half an hour of isolation.

Tissue Engineering of Vessels

Tissue-engineered porcine arteries were created by seeding five million porcine carotid smooth muscle cells onto a tubular polyglycolic acid mesh (3 mm in diameter and 8 mm in length; Concordia Medical, Coventry, R.I.) around a silicone tube and cultured in a bioreactor connected to a peristaltic pump at 5% $CO_2$ and 37° C. The engineered vessels were harvested from bioreactors after 8 weeks of culture and rinsed two to three times with PBS to remove traces of culture medium. Within half an hour of isolation, tissues were subjected to decellularization.

Decellularization Procedure of Both Rat Aortas and Tissue Engineered Vessels

Decellularization was accomplished using a detergent-based method that included incubation in CHAPS/SDS buffer (8 mM CHAPS, 1 M NaCl, and 25 mM ethylenediaminetetraacetic acid (EDTA), 1.8 mM SDS, 1 M NaCl, in PBS) for 24 hours, followed by a 2-day wash with PBS to completely remove the detergent. Finally, aortas and/or tissue engineered grafts were incubated in PBS containing 10% (v/v) FBS (Hyclone, Logan, Utah) and 1% Penicillin/Streptomycin (Pen/Strep). All decellularization steps were carried out at 37° C. with agitation under sterile conditions. Decellularized vessels were stored in PBS containing 1% Pen/Strep at 4° C. for up to 2 weeks.

Coating Protocol

The decellularized vessels were mounted on in-house built closed loop perfusion chamber via end-ligation of the vessels onto capped needles. Before coating the vessels, they were perfused with 5% Pen/Strep in PBS solution. The SM(PEG)n NHS-PEG-Maleimide Crosslinker (Thermo) (100 mg) equilibrated to room temperature, was dissolved in 187 µl DMSO by vortexing followed by 2 min sonication step. When the crosslinker-DMSO solution was clear, 3 ml of PBS were added and total solution was immediately perfused into the vessel via the 3-way stopcock. The crosslinker solution was perfused back inside the vessel via a second loop, creating a continuous perfusion in a loop fashion for 30 min. The excess crosslinker was rinsed out of the vessel by open-end perfusion of the vessels with 100 ml of PBS. Rinsing was not done for more than 15 min as the thiol-reactive groups of the attached crosslinker reacted with the water in PBS. The thiol-modified hyaluronic acid (Glycosan, San Francisco, USA) was then dissolved in 1 ml of degased water without uncapping the vial. The vial was placed on rotating plate for 30 minutes to fully dissolve. Two milliliters of the reconstituted thiol-modified hyaluronic acid were perfused into the vessel over the course of 2 hours in a closed loop fashion. After 2 hours, the excess thiol-modified hyaluronic acid was removed by syringe aspiration inserted into the 3-way stopcock. The vessel was then rinsed for 2 hours with 500 ml of PBS in a one loop fashion removing unreacted but bound hyaluronic acid.

If a rougher morphology was desired, cleaned vessels were perfused with 5 ml of Hylaronidase (300 µg/ml)/collagenase (0.5 mg/ml) mixture at 37° C. for 2 hr. After perfusion of the Hylaronidase/collagenase mixture, the vessels were rinsed with 200 ml of PBS via open-end perfusion.

ADH-amino modified heparin was prepared by adding heparin (100 mg, 8.3 µmol) into 10 mL of formamide and heating at 50° C. After heparin was totally dissolved (about 30 mins), adipic acid dihydrazide (ADH) (10 mg, 92 µmol) was added. The reaction was maintained at 50° C. for 6 h. Aqueous sodium cyanoborohydride (9.5 mg, 150 µmol) was then added and the mixture was incubated at 65° C. for an additional 24 h. The reaction mixture was diluted with 50 mL of water and dialyzed against 2 L of water for 48 h using a 3500 molecular weight cutoff (MWCO) dialysis membrane. The retentate was recovered, lyophilized, and purified by ethanol precipitation Amino-modified heparin (120 mg) was dissolved in 16% w/v NaCl/MES buffer at pH 7. EDC (110 mg) and NHS (78 mg) was dissolved in 10 ml 16% w/v NaCl/MES buffer at pH 5 and perfused through the vessel for 15 mins. (pre-activating carboxyls of collagen). The excess EDC/NHS was rinsed by 50 ml perfusion of MES buffer at pH 7. The dissolved heparin was then perfused through the vessels for 1 hr. The excess unreacted heparin was washed by perfusion with 500 ml of PBS.

Characteristics of HA and HA-Heparin Coatings

The crosslinking of HA onto decellularized aortas using the aortas amine groups and HA thiol groups via NHS-maleimide $SM(PEG)_{12}$ crosslinker was optimized to 40 mM $SM(PEG)_{12}$ crosslinker concentration for a full coverage of the decellularized structures. The surface accessible carboxyl groups available on the HA layer for the heparin addition step was assessed via nanoparticles (NPs) tagging. As indicated by the NPs at 40 mM $SM(PEG)_{12}$ concentration, an abundance of free carboxyl groups remain on the surface of the HA coating.

Figure 4:
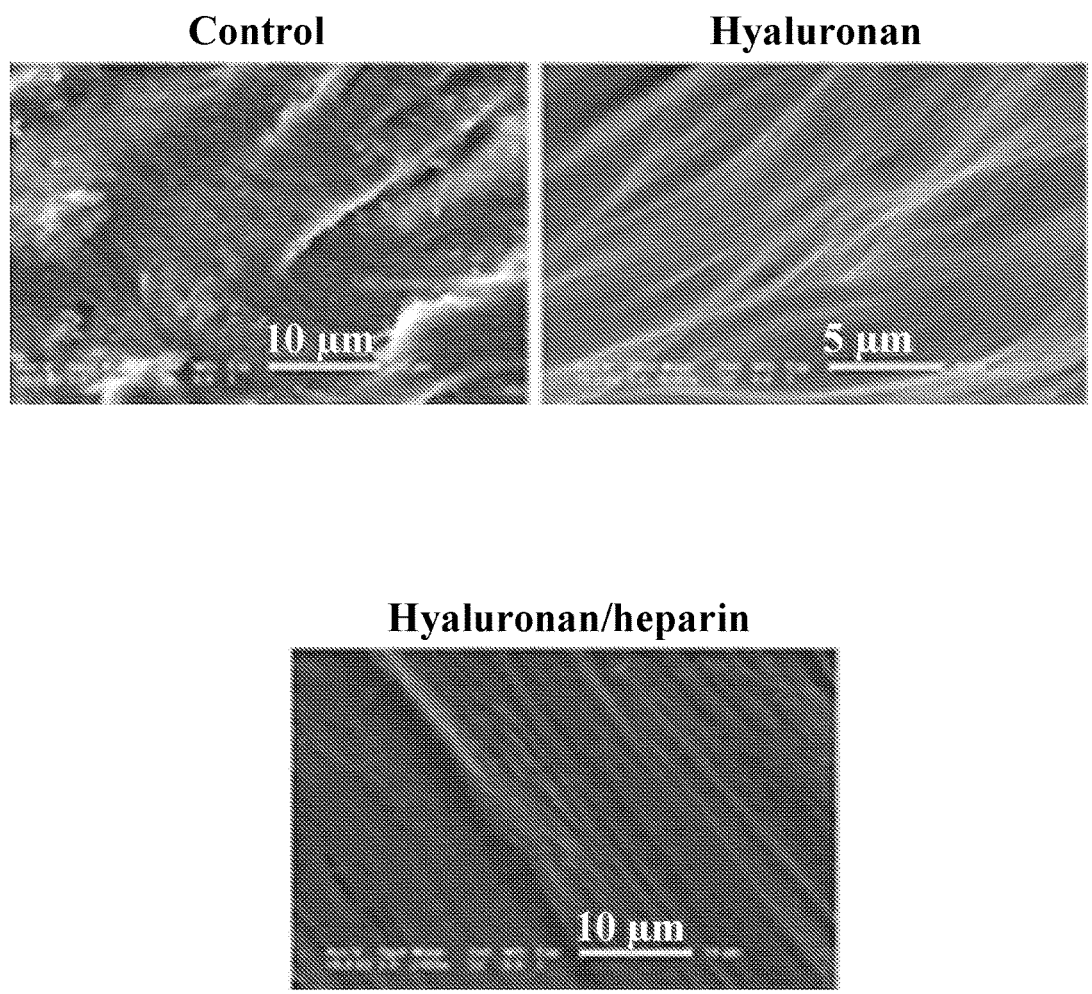
FIG. 4 is a set of images depicting the birds-eye view SEM images of control decellularized rat abdominal aortas (aortas that are decellularized with no further treatment), hyaluronic acid coated decellularized aortas, and layer-by-layer hyaluronic acid-heparin coated aortas.

Tubular decellularized rat abdominal aortas were coated in a closed loop perfusion. The morphological changes in the vessel luminal side were obvious in scanning electron microscopy (SEM) images, as shown in FIG. 4. The control-decellularized aortas (luminal diameter about 3 mm) have a rough appearance due to the decellularization detergent washes necessary for cellular removal. HA crosslinking via $SM(PEG)_{12}$ onto the vessels surface resulted in a smooth vessel surface. The "end-on" crosslinked heparin layer on top of the HA layer restored the rougher appearance of the vessel.

Figure 5:
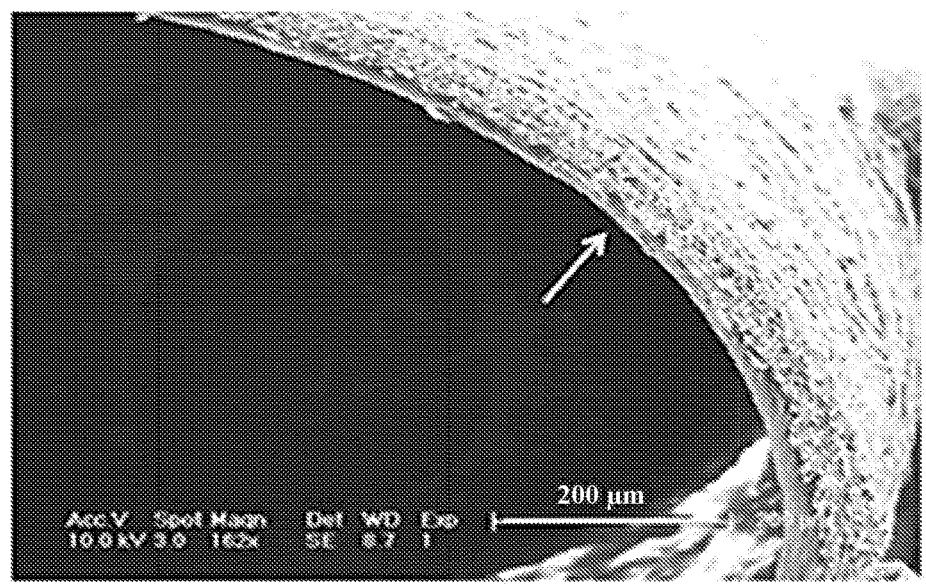
FIG. 5 is an image depicting a SEM cross-section of entire tubular decellularized rat abdominal aortas layer-by-layer HA-heparin coated. The coating can be clearly seen on the luminal side of the vessels as a few microns thick layer as indicated by white arrow.

A SEM cross-section of the decellularized rat abdominal aortas layer-by-layer HA-heparin coating showed that the coating extending luminally in the aorta. As shown in FIG. 5, the coating was observed as a smoothed structure coating the porous vessel.

Figure 6:
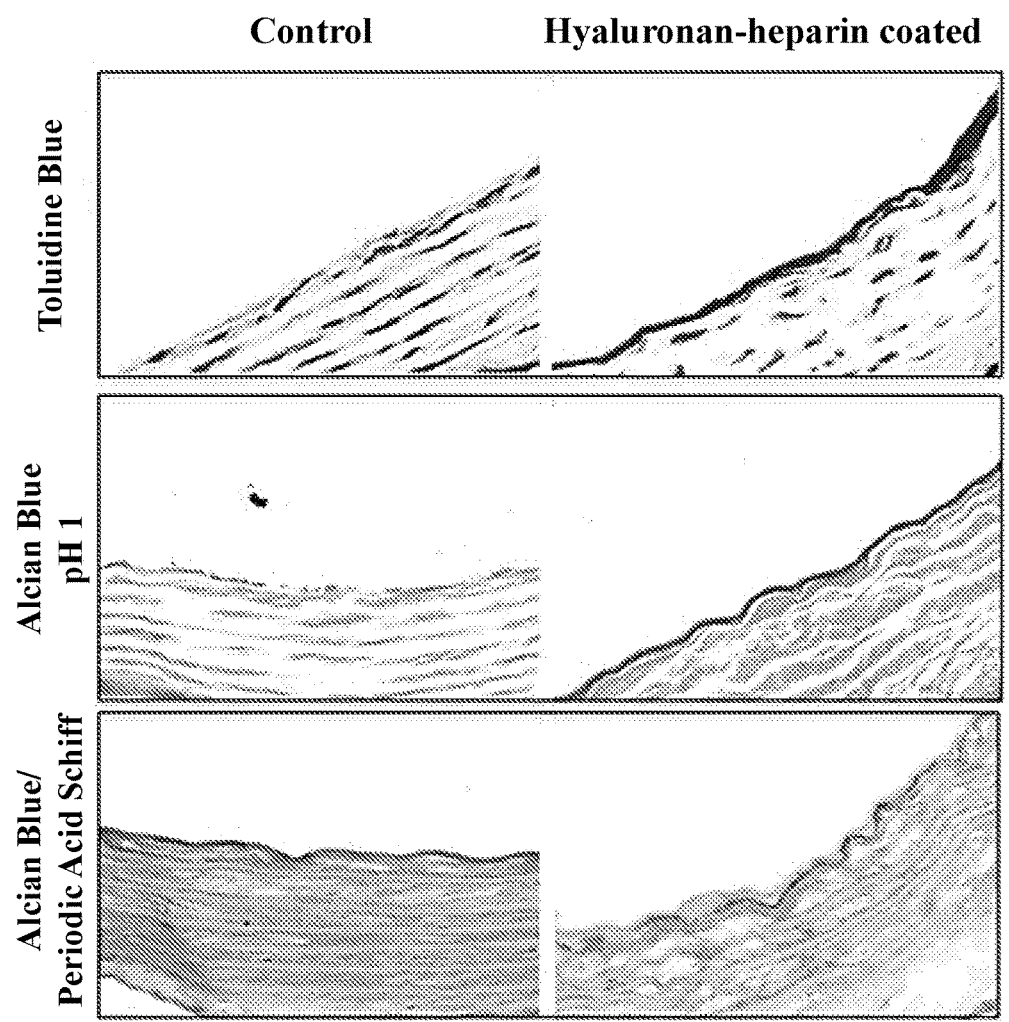
FIG. 6 is a set of images depicting histological sections of entire tubular control rat abdominal aortas (decellularized aortas with no further treatment), and layer-by-layer hyaluronic acid-heparin coated decellularized aortas. The sections were stained with Toluidine Blue, Alcian Blue pH1, and Alcian Blue PAS. The coating can be clearly seen on the luminal side of the vessels as a few microns thick layer.

Histological analyses of layer-by-layer coated vessels cross-sections were performed with Toluidine Blue, Alician Blue, and Alican Blue/PAS. Toluidine Blue is a basic dye attracted to negatively charged structures such as heparin. Alcian Blue and Alcian blue/PAS cationic dyes are also attracted to negatively charged structures under alkaline conditions. As shown in FIG. 6, all three dyes stained the HA-heparin coating strongly.

Figure 7:
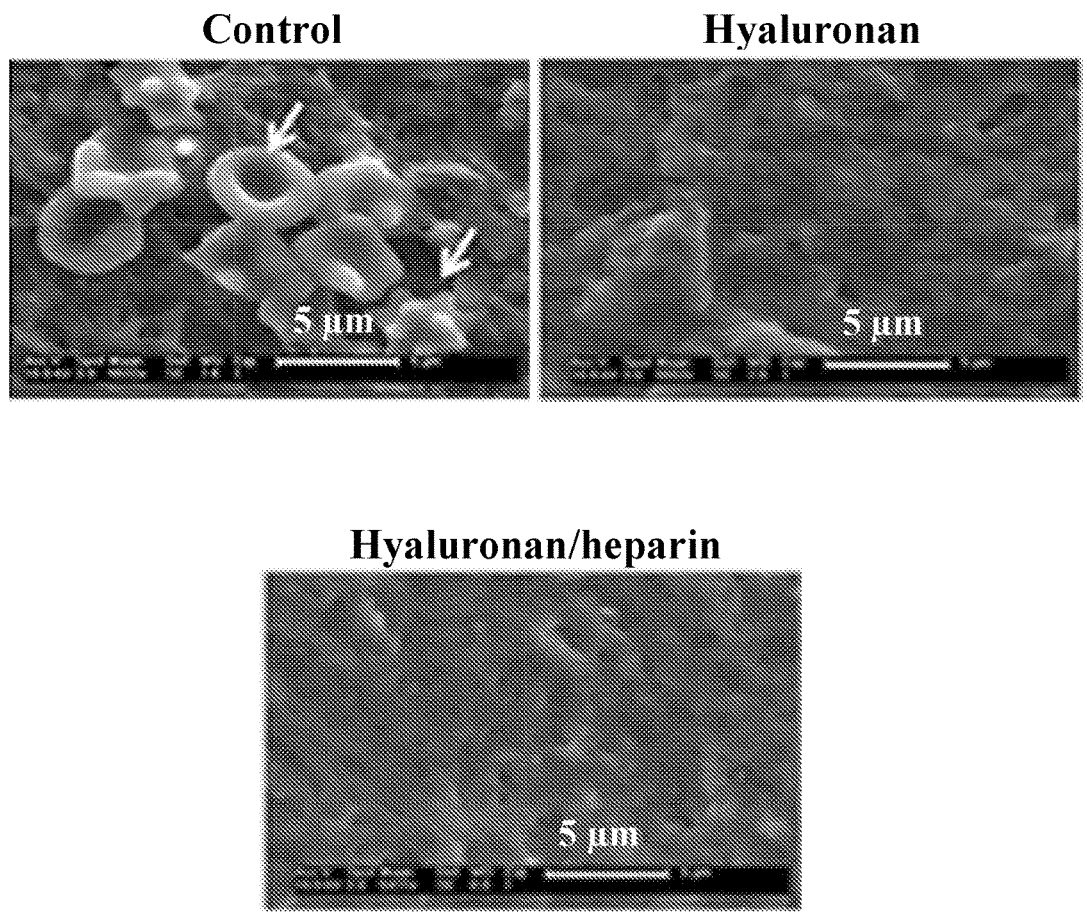
FIG. 7 is a set of SEM images of platelets isolated from rat blood incubated on decellularized control rat abdominal aortas, hyaluronic acid coated and layer-by-layer hyaluronic acid-heparin coated decellularized aortas. The platelets and thrombus formation are clearly visible on the control. The treated vessels show complete absence of platelets adhesion.
Figure 8:
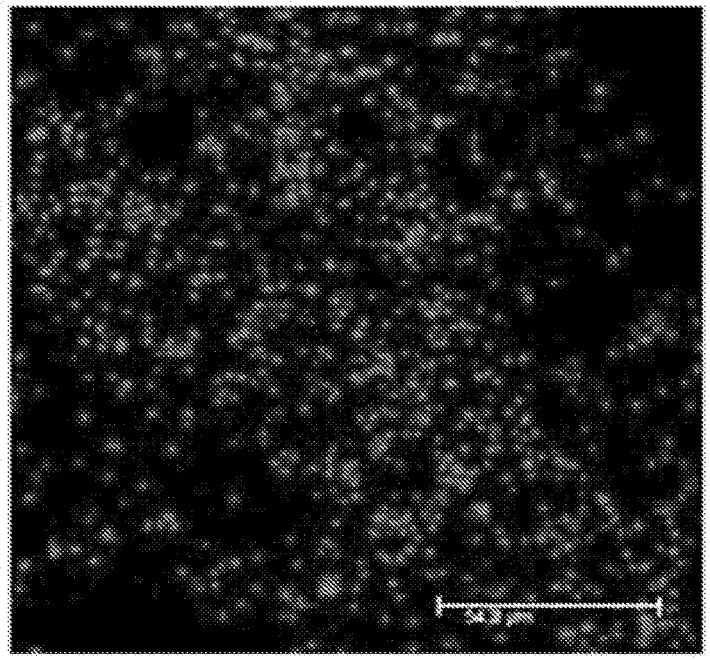
FIG. 8 is a set of images depicting the results from experiments where platelets were phalloidin stained (which produces a red color in the platelets), incubated on decellularized control rat abdominal aortas, and layer-by-layer hyaluronic acid-heparin coated decellularized aortas. The platelets are clearly visible on the control aorta. The coated aortas show an absence of platelets.
Figure 8:
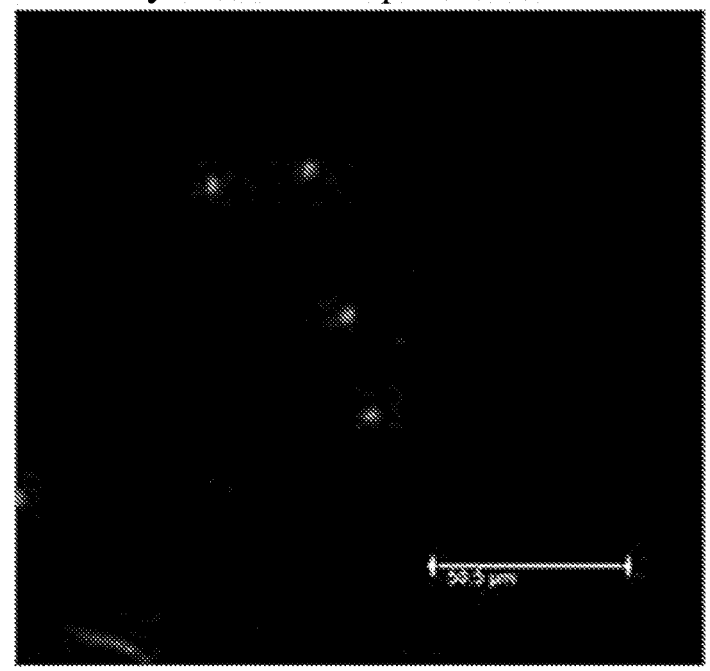

To assess the thrombogenic effects of the coatings, isolated blood platelets were incubated under constant agitation on the surface of decellularized, HA-coated and HA-heparin coated vessels. As shown by the SEM images in FIGS. 7 and 8, platelets strongly adhered to uncoated decellularized vessels and the surface of the uncoated decellularized vessels were densely covered in platelets and red blood cells. Decellularized vessels contain abundant collagen on the surface, which is a potent activator of platelets, and thus uncoated decellularized vessels are thrombogenic. In comparison, both HA and HA-heparin coated vessels strongly resisted platelet adhesion. In fact, it was hard to find any platelets on the surface of the coated vessels.

Figure 9:
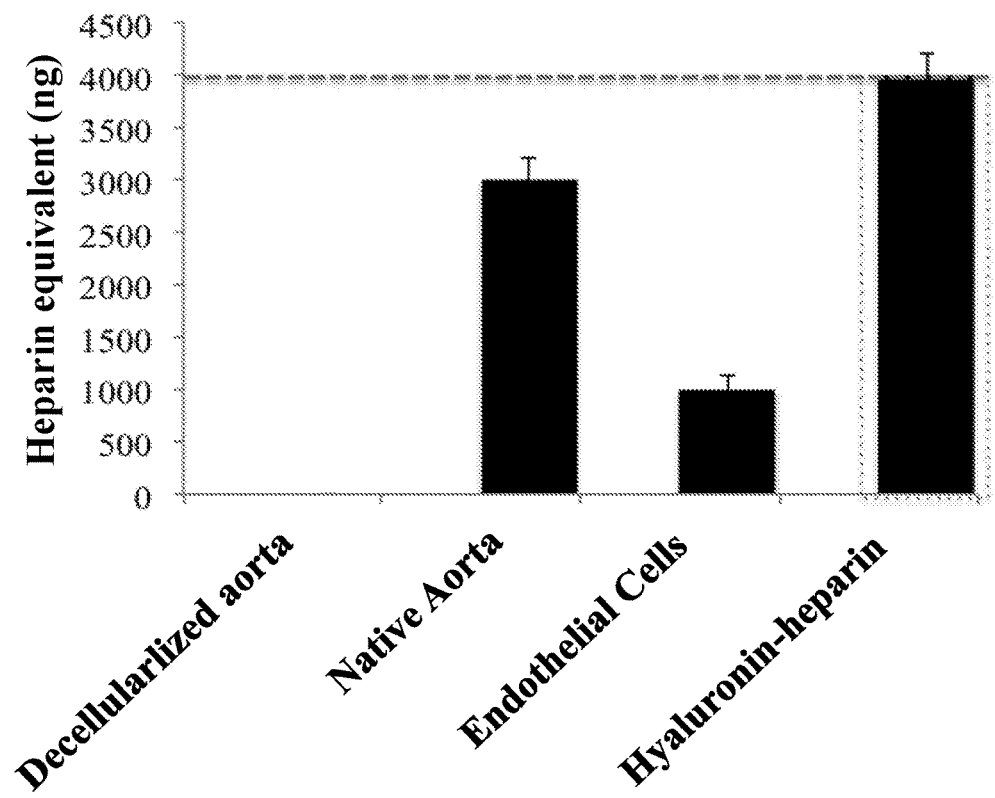
FIG. 9 is a graph depicting the determination of functional surface heparin via the Factor X assay where the heparin effects on Factor X inactivation are expressed in back-calculated heparin equivalent weights. The assayed samples were: decellularized control rat aortas, freshly excised native rat aorta with a continuous layer of endothelial cells preserved, a cultured continuous monolayer of HUVECs, and decellularized rat aortas hyaluronic acid-heparin coated.

To assess the amount of immobilized functional heparin on the HA layer, the Factor X assay was utilized. It was a method based on the conformational change of antithrombin III by bioactive heparin, resulting in factor Xa inhibition. The Factor X inhibition was then measured by S-2732 Chromogenic substrate (Suc-Ile-Glu(g-Pip)-Gly-Arg.pNA), and functional heparin was assessed by comparison with Heparin standards (0-100 ng) reacted in the same manner as the scaffolds. The capacity of a surface to inactivate Factor X was strongly correlated with the surface capacity to delay the blood coagulation cascade. In comparison with freshly excised native aorta lined by functional endothelial cells to retard coagulation, the HA-heparin coated decellularized aortas showed at least as much active heparin, which inhibits Factor X activity (FIG. 9). Decellularized control aortas were highly thrombogenic and did not demonstrate any heparin activity, as demonstrated by very low Factor X inactivation (see FIG. 9). A continuous monolayer of human umbilical vein endothelial cells (HUVEC) grown for 5 days which was known to demonstrate anticoagulant activity demonstrated lower anti Factor X activity than the HA-heparin coatings.

Figure 10:
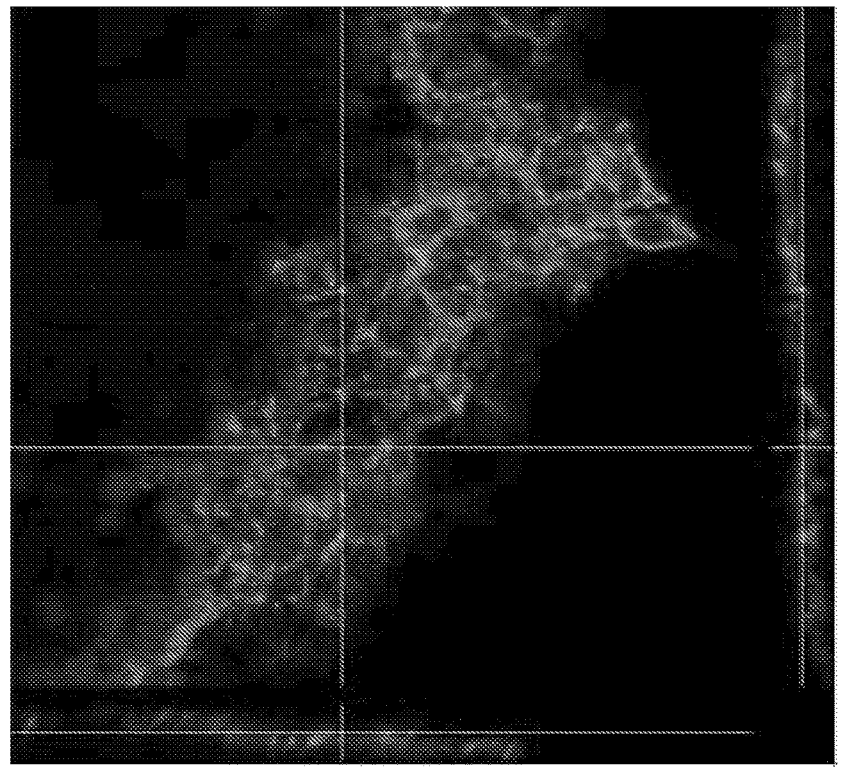
FIG. 10 is an image depicting the results of experiments wherein HUVECs were plated on HA-heparin layer-by-layer coated aortas and cultured for 2 weeks. The HUVECs cytoskeleton was stained with phalloidin (red) and HUVECs nucleus was stained with DAPI (blue) and imaged over a 10 μm z-stack. The x and y axis are shown on the sides of the image where the HUVECs are seen growing a non-planar monolayer. The HUVECs can be seen invading the coating.

To assess the potential toxicity of these coatings, human umbilical vein endothelial cells (HUVECs) isolated from human umbilical cord were seeded onto the HA-heparin layer-by-layer coated aortas and cultured for 2 weeks. The HUVECs proliferated over the coating surface but also invaded the coating by degrading it over the course of the two weeks. The HUVECs downward invasion into the coating could be seen from the confocal microscopy image (FIG. 10), where inward migrating HUVECs were shown over a 10 µm z-stack.

Experiments were also performed to examine whether the coatings produce inflammatory responses, stimulate recruitment of monocytes and macrophages, or stimulate adhesion and invasion of leukocytes. Further, experiments were done to determine whether grafts coated with these coatings became luminally coated with host endothelial cells after implantation into the vascular system. Further, experiments were conducted to determine if the HA layer or heparin layer bound to growth factors that were conducive to the cellular repopulation of the grafts. Finally, experiments were performed to determine if the coatings were resistant to intimal hyperplasia, a common mid-term to late-term failure mode for arterial grafts.

The data described herein demonstrated HA and HA-heparin coatings served as anti-thrombogenic coatings for biological scaffolds including decellularized vascular grafts. The coating described herein utilized the crosslinking of HA to protein substrates of the decellularized tissue. Further, the layer-by-layer coating of heparin on HA enhanced the immediate anti-coagulant properties. The HA layer offered a physical barrier to thrombogenic collagen, other extracellular matrix proteins, or synthetic materials which stimulated the extrinsic or intrinsic coagulation cascade, while the layer of active heparin was attached in its active conformation with an exposed pentasaccharide sequence free to interact with blood components.

It was demonstrated that coating with HA alone inhibited coagulation as evidenced by attenuation of platelet adhesion/activation and inactivation of Factor X and thrombin activity. Thus, HA coatings may be efficacious for small caliber grafts (i.e., less than or equal to 6 mm in diameter). Further, HA-coated grafts displayed higher mechanical properties as measured by increased suture strengths that were conferred by the mechanical characteristics of the coating. The data also demonstrated that HA-coatings and HA-heparin layer-by-layer coatings were highly conducive to cellular ingrowth. Therefore, as presented herein, HA coatings and layer-by-layer HA-heparin coatings served as functional anti-thrombotic coatings of vascular grafts.

In order to more fully characterize the process of gel formation on the surface of collagen-containing grafts, the time of gelation of the PEG crosslinker and hyaluronic acid (HA) was evaluated at 25° C. via a strain-controlled rheometer (ARES LS1, TA Instruments, New Castle, Del.). A porcine decellularized aorta was mounted onto the titanium cone of the apparatus, followed by the incubation of 400 µl of PEG crosslinker for 45 mins. After this, the PEG crosslinker was aspirated, and 1000 µl of HA was loaded on top of the decellularized porcine aorta (these steps mimicked the 3D perfused coating). Finally, the decellularized porcine aorta-HA gel complex was closed with the stainless plate of the apparatus (25-mm diameter, 0.04-radian angle, 45-µm gap). As a control, the HA gels were deposited onto decellularized porcine aorta without the addition of the PEG crosslinker step, and the system was closed with the stainless plate in the same way. Elastic (G') and loss (G") moduli (1% strain, 1 Hz) were recorded every 9 s for 24 h. The complex shear modulus (storage modulus) G of the HA-PEG gels and HA gels alone was calculated from:

$$G = \frac{Td}{2I_p\gamma}$$

where T was the torque response, d was the sample diameter, $\gamma$ was the sinusoidal shear strain, and $I_p$ was the polar moment of inertia of the cylinder ($I_p=\pi d^4/32$).

Figure 11:
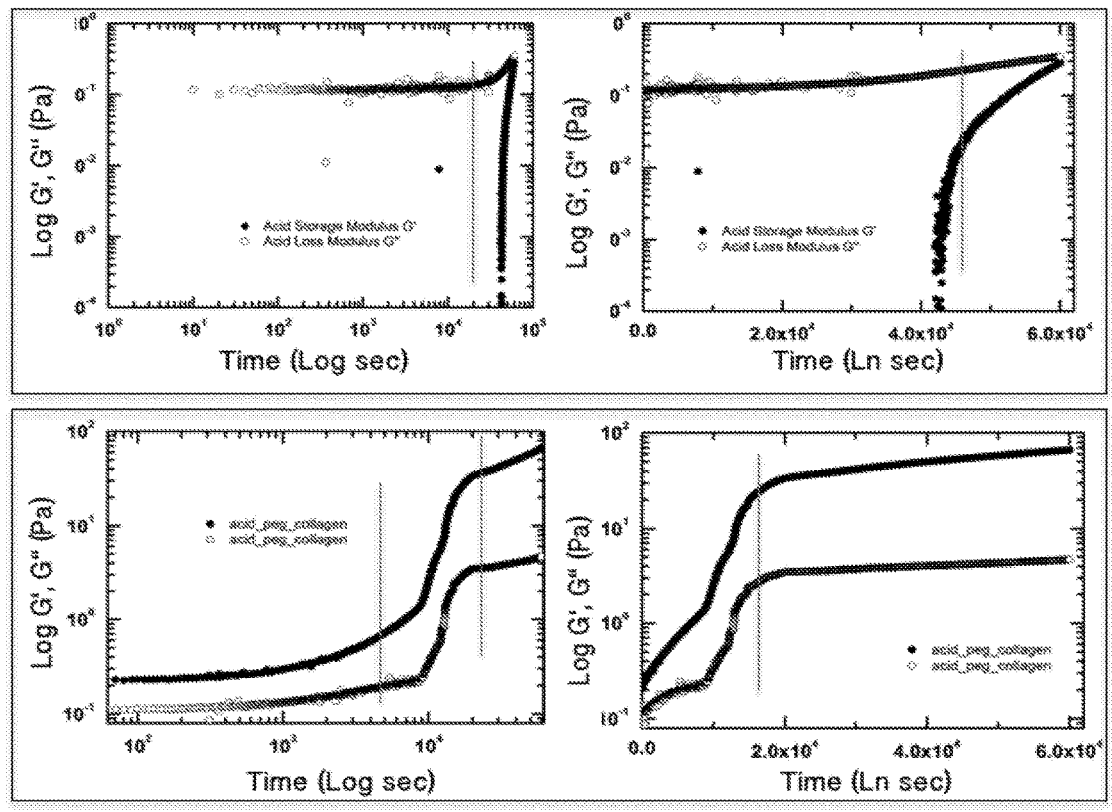
FIG. 11 is a panel of graphs showing storage modulus (G' full circles) and loss modulus (G" open circles) of HA gels and HA-PEG crosslinker incubated onto decellularized porcine aorta plotted as a function of time. Panels A and B display the Hyaluronic acid loaded onto decellularized porcine aorta in the absence of the PEG crosslinker and where the elastic (G') and loss (G") moduli are plotted against time in Log (panel A) or Ln (panel B). Panels C and D display the Hyaluronic acid loaded onto decellularized porcine aorta with the addition of PEG crosslinker. The elastic (G') and loss (G") moduli are plotted against time in Log (panel C) or Ln (panel D). The storage modulus G was calculated to be 37 kPa for the HA-PEG and 2 kPa for the HA gels without the PEG crosslinker at 80% polymerized form of the gels using the complex storage modulus equation above. Of importance to the coating developments, the HA-PEG gels attain their mature cross-linked form within 4 hours of incubation and the HA gels alone attain a mature form within 23 hours of incubation. This indicated that after at least 4 hours of luminal perfusion of the HA gels within the vessels should have fully polymerized coatings.

As can be seen in FIG. 11, the rheological response to imposed oscillatory shear stress of the HA gels on the decellularized aorta in the absence of the crosslinker was a fluid-like initial response that polymerized to 80% of the added volume after 23 hours. This was shown in panel A and the 23 hours were indicated by the red dotted line intersecting the x-axis of log time at $5\times10^4$ sec. When transforming the time frame from a Log scale into a Ln scale (Ln scale plotted in panel B), the polymerization of HA component alone on the decellularized graft resulted in the same time frame of 23 hours to gain 80% polymerization.

The addition of the PEG crosslinker on the decellularized aorta activating the amine groups before the addition of the HA component induced 80% polymerization of the HA layer within 4 hours of incubation. This was evident in both panels C and D where in both Log time and Ln time plots (respectively) of the storage modulus (G") with respect to time becomes constant at panel C $10^4$ sec (log scale). The addition of the PEG crosslinker on the decellularized aorta activating the amine groups before the addition of the HA component induced 80% polymerization of the HA layer within 4 hours of incubation. The absence of large magnitude changes in the viscous (G") and elastic (G') properties after 4 hours is indicative of no further microstructural change in the HA gel component indicating that HA preceded by PEG attains its 'mature' form within 4 hours. The 80% polymerization in all cases was estimated roughly as the place where no further microstructural changes were evident from the constancy in storage modulus with respect to time. This was identified in all panels with a red dotted line.

The rheological characterization thereby described set the perfusion time of the HA component onto the decellularized vessels to create the coating to a minimum perfusion time of 4 hours to a maximum perfusion time of 18 hours.

To asses the stability of the coatings, porcine and rat aorta, as well as tissue engineered vascular grafts, were decellularized and coated both with Hyaluronic acid (HA) alone and Hyaluronic acid/Heparin (HA/HP). The example shown here was from rat decellularized abdominal aortas but the various studied vasculature structures behaved similarly.

The stability of HA and HA/HP coatings was evaluated at 37° C. over two weeks by incubating the coated decellularized vessels under the following conditions: 1) PBS; 2) M199 cell culture medium; and 3) freshly isolated rat blood plasma obtained by filtering freshly drawn rat blood through 0.2 µm syringe filters. Following the above described incubations, the eluted coating was assessed by quantifying the total amount of polysaccharides in solution at Day 1, 3, 7 and 14 using the Carbazole assay. The Carbazole assay quantifies polysaccharides in solution based on colorimetric changes with a detection limit of 2 µg/ml.

The amount of released HA and HA/HP from the various coated decellularized surfaces was comparable to the amount of polysaccharides released from the uncoated decellularized vessels (stable negative control samples). For instance the highest amounts of detected released polysaccharides from the coated surfaces was of 0.2 µg/ml which was the amount of polysaccharides released by the non-coated decellularized vessel used as negative control and it also was below the Carbazole assay detection limit. The low polysaccharides released into solution over time indicated high stability of the coating under in vitro physiological conditions.

Figure 12:
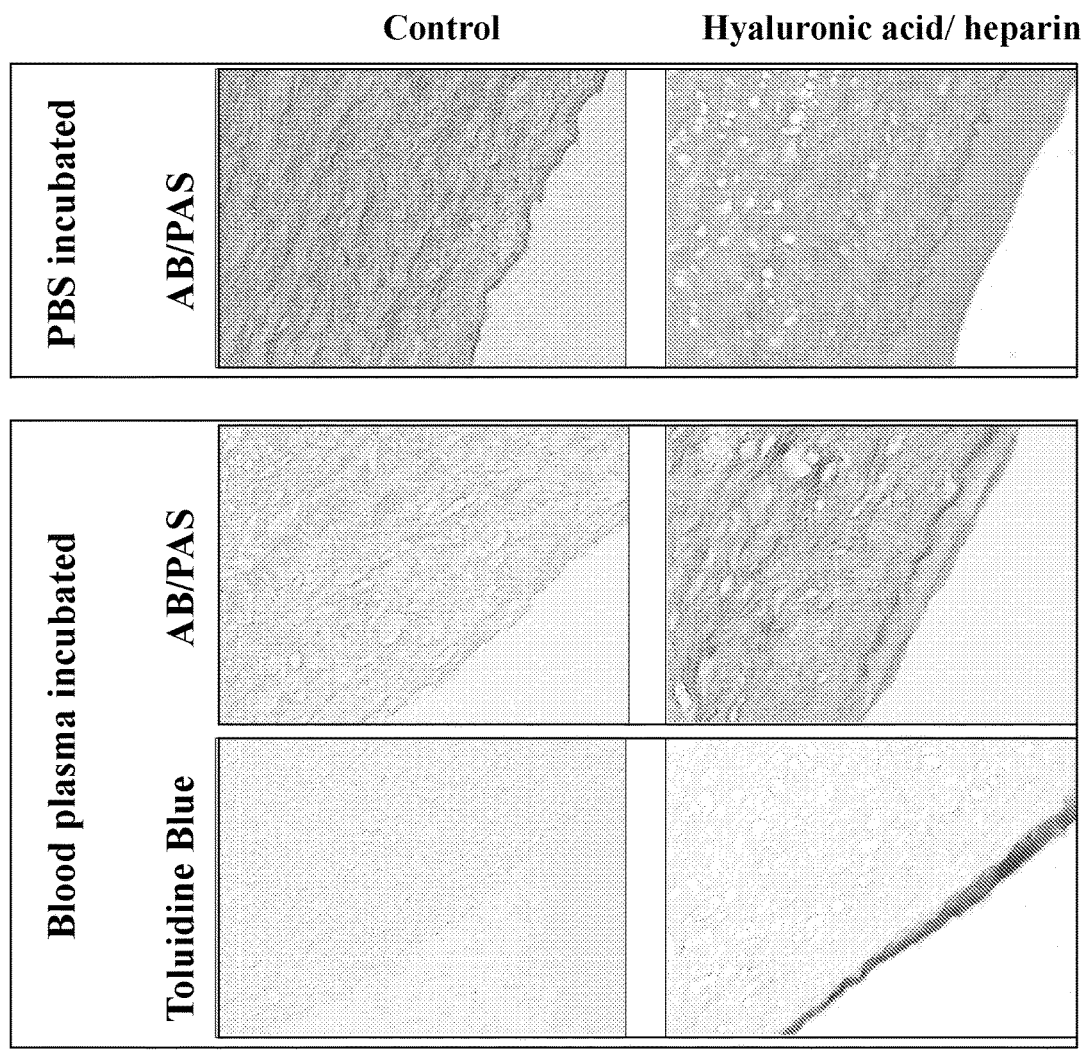
FIG. 12 is a panel of images showing decellularized rat aortas uncoated control (left-hand panel of images) and decellularized rat aortas Hyaluronic Acid/Heparin coated (right-hand panel of images) stability evaluation at 37° C. for two weeks incubated under PBS (panel A) and freshly drawn rat plasma (panel B). Following both PBS and rat plasma incubation the coating remains present and visible via AB/PAS and Toluidine Blue stains.

Following the two weeks incubation time, the coated decellularized grafts were histologically assessed for remaining coating on the decellularized vessels using Toluidine Blue, and Alican Blue/PAS dyes. As shown in FIG. 12, following PBS incubation at 37° C. for two weeks the Hyaluronic acid/Heparin coated decellularized rat aortas kept a continuous layer of the coating in place. This was especially evident in comparison with the uncoated (control) decellularized rat aortas where only the background stain of the decellularized aorta was present. In addition, after two weeks incubation with freshly drawn rat blood plasma (changed every three days) the Hyaluronic acid/Heparin coating layer also remained visible on the decellularized rat aortas as seen by Toluidine Blue, and Alican Blue/PAS stains. This observation suggested that blood enzymes did not degrade the coating in its entity in two weeks time.

Figure 13:
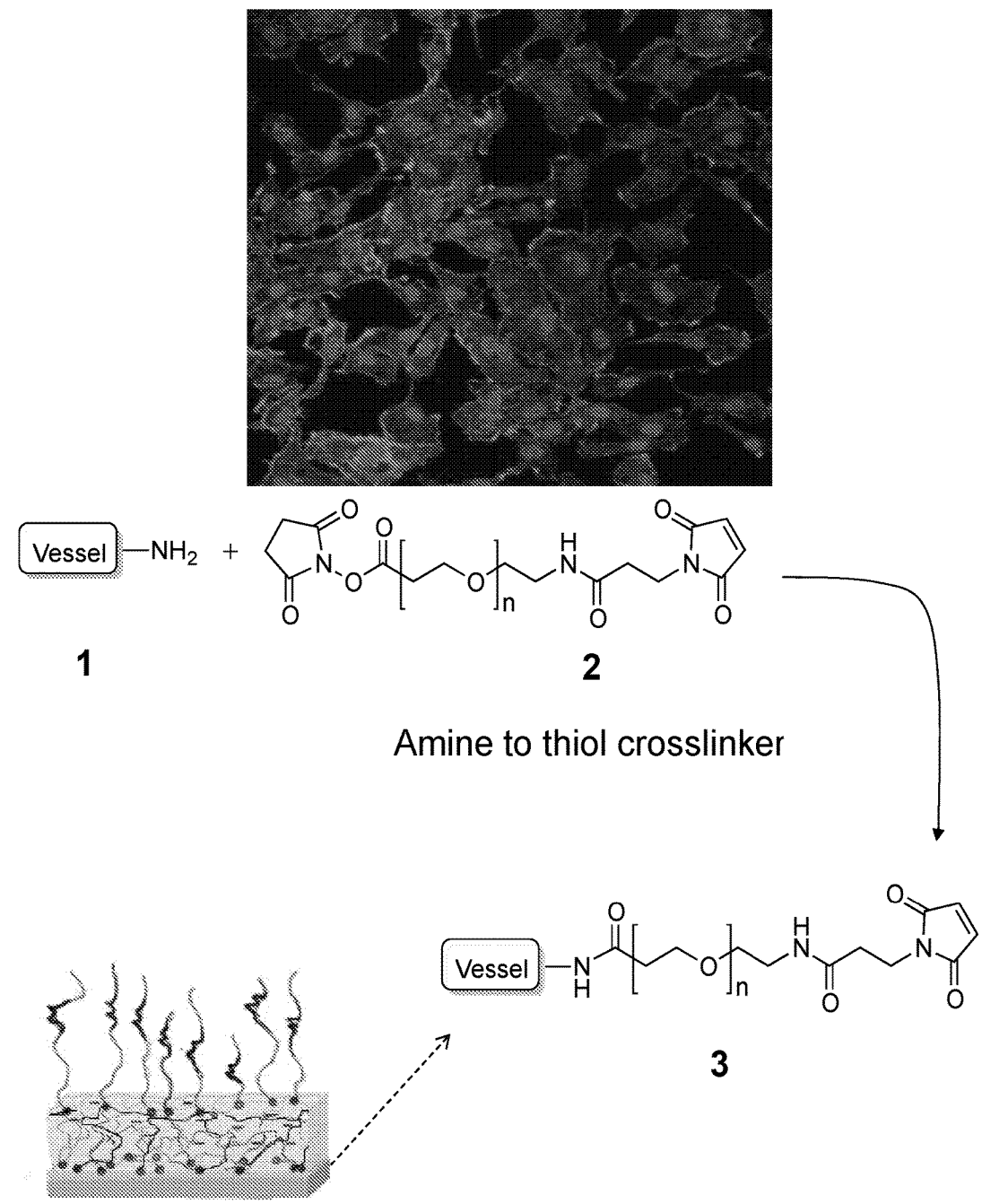
FIG. 13 is panel of images showing HUVECs seeded onto the three different coating layers deposited stained with DAPI (blue) and VE-Cadherin (red) after three days of culture. The coating components are biocompatible and support endothelial cell growth and proliferation in vitro on short time periods.

The endothelial cell growth response on the individual coating layers was evaluated. A PEG crosslinker layer alone, PEG crosslinker and Hyaluronic acid layer, and lastly the PEG crosslinker-Hyaluronic acid and heparin components combined were coated. After gelation, each of these systems was seeded with freshly isolated human umbilical vein endothelial cells (HUVECs) and cultured for three days. FIG. 13 shows the day 3 cultured HUVECs that were stained with DAPI for nuclei (FIG. 13), and VE-Cadherin for an endothelial membrane surface marker (FIG. 13). It was seen that the various layers of the coating supported endothelial cell adhesion and proliferation in vitro. Certain areas of the coating had less dense cell coverage than other areas, as the cell coverage was not uniform throughout the coating.

Rat aortas from the thoracic and abdominal portion were harvested and decellularized. The decellularized rat aortas were implanted in three rats without further modification (control group) and three decellularized rat aortas were Hyaluronic Acid coated prior to implantation, using the steps of applying the PEG crosslinker followed by thiolated HA to form a gel on the luminal surface of the decellularized aortas. The rat implantation was done by first clamping the proximal and distal portions of the infrarenal aorta and removing a 17-mm segment of aorta that was replaced by decellularized rat aorta untreated (control group) or Hyaluronic Acid-coated decellularized rat aorta. The grafts were inserted by end-to-end anastomosis using interrupted 9-0 monofilament nylon sutures. Following the suturing of the grafts in place the distal and then the proximal vascular clamps were slowly removed, and flow was restored through the graft. The graft patency was monitored by color Doppler imaging and pulse waves recorded with a 12-MHz sector probe and an echo-imaging apparatus at 2 and 4 weeks. Graft diameter and blood flow velocity were measured. Signs of thrombosis and aneurysm formation were carefully checked. The rats were sacrificed after four weeks and the grafts were evaluated histologically by staining segments of the grafts using hematoxylin and eosin (H&E) for general evaluation.

Figure 14:
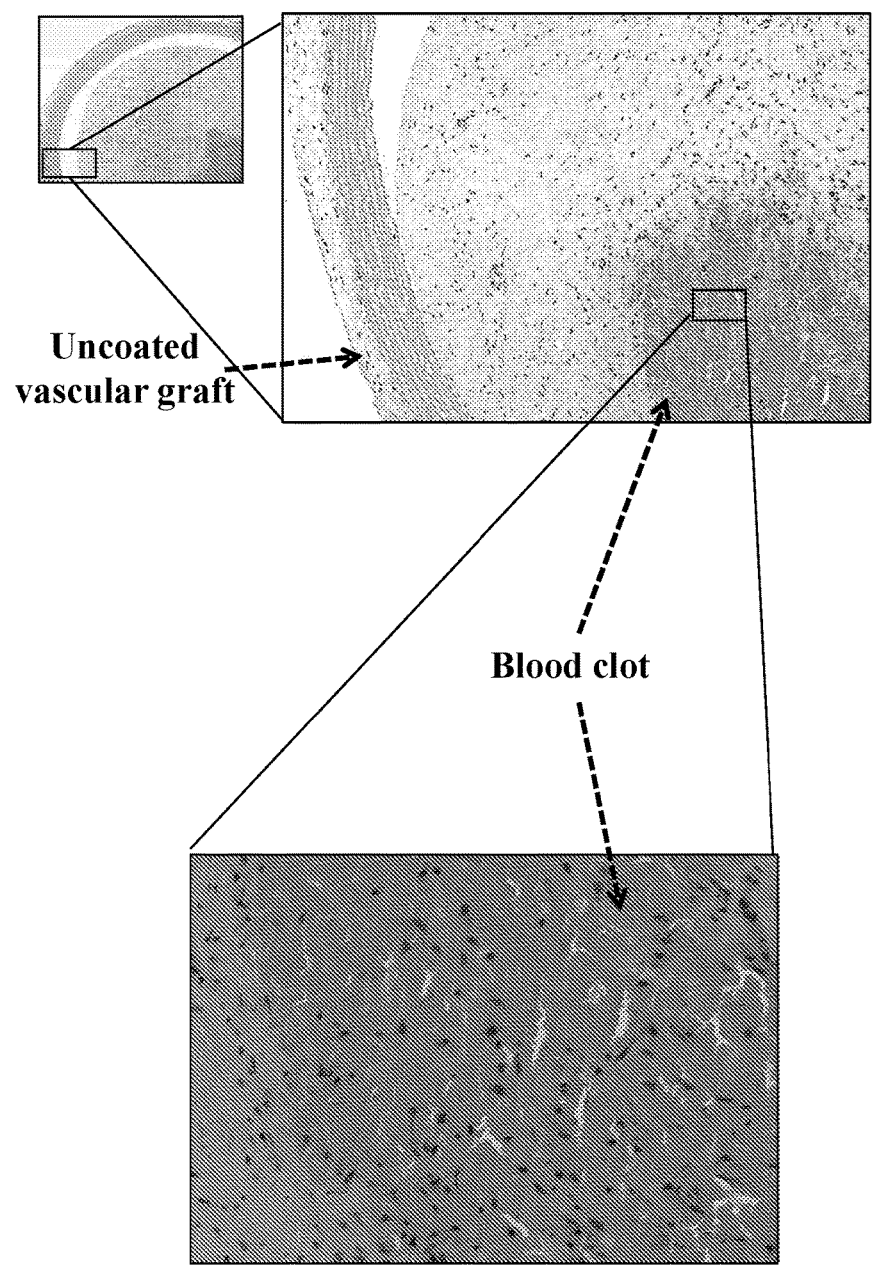
FIG. 14 is a panel of images showing cross-sections of rat-decellularized grafts implanted end-to-end in rat abdominal aortas at after 4 weeks of implantation. The top panel shows an example of the control group where the implanted graft was a decellularized rat aorta without further modification. The bottom panel shown an example of Hylaronic acid coated rat decellularized graft implanted end-to-end in rat abdominal aorta 4 weeks after implantation. All the sections were stained with hematoxylin and eosin (H&E) showing the migration of abluminal cells within the grafts and the cellular deposition within the large blood clot of the control group rat.

Uncoated decellularized grafts (control groups) shown in FIG. 14 top panel formed large clots with large amounts of fibrin deposition that almost fully occluded the blood flow of the abdominal aorta. The H&E staining was showing the large fibrinized blood clot that was covering almost the entire luminal opening of the implanted graft. The Doppler ultrasound recording of the blood flow at four weeks post-implantation was showing no recording of the blood flow. In some rats there was total absence of blood flow and in other there was some minimal blood flow of about 3 cm/s. On the other hand, the Hyularonic acid coated decellularized rat aorta demonstrated absence of blood clots in most rats as was shown in the H&E stained cross section of the bottom panel in FIG. 13. Some rats showed small to medium sized clots deposition and some occlusion of the implanted aorta. The Hyaluronic acid coating was visible in the explants on some areas of the lumen (shown in FIG. 14 bottom panel) but the thickness of the coating was greatly reduced. The Hyaluronic acid coated decellularized rat aortas demonstrated normal blood flow at the time of explantation of 4 weeks as was shown in FIG. 15 bottom panel. The explants were not dilated and resembled in appearance as pre-implantation. On most areas, the implants were abluminally integrated within the surrounding tissues. Staining for T-cells and macrophage markers has revealed no conclusive signs of inflammation reactions in the implants.

Hyaluronic acid coated decellularized vascular rat aortas implanted in the rat animal model suggested clinical feasibility of hyaluronic acid coated vascular grafts.

Tissue engineered vascular grafts (TEVG) were grown as per established protocols starting with dog harvested smooth muscle cells. Grafts were 4 mm diameter and approximately 5 cm in length. TEVG were decellularized as described previously in patent. In the control group, the decellularized TEVG were implanted without further modifications; and the second animal group received Hyaluronic acid and heparin-coated decellularized TEVG. The dog study used longer grafts than the rat animal study (implanted grafts were about 5 cm in length), and the implantation site of carotid artery was chosen as a more aggressive animal model than the rat abdominal aorta.

The implantation surgery was performed by first identifying and dissecting the dog carotid arteries free from surrounding tissue. One centimeter of the carotid artery was removed and a Hyaluronic acid-heparin-coated decellularized TEVG (4-mm internal diameter) was implanted into the right carotid artery using end to side anastomoses. The non-coated decellularized TEVG (4-mm internal diameter) was implanted in the left carotid artery by the same procedure. The internal diameter of the vascular grafts closely matched with the recipient carotid arteries. The patency of all vascular grafts was checked by Doppler ultrasound immediately after implantation. The implants were kept in the dogs for four weeks, at which time they were explanted and histologically examined.

Figure 15:
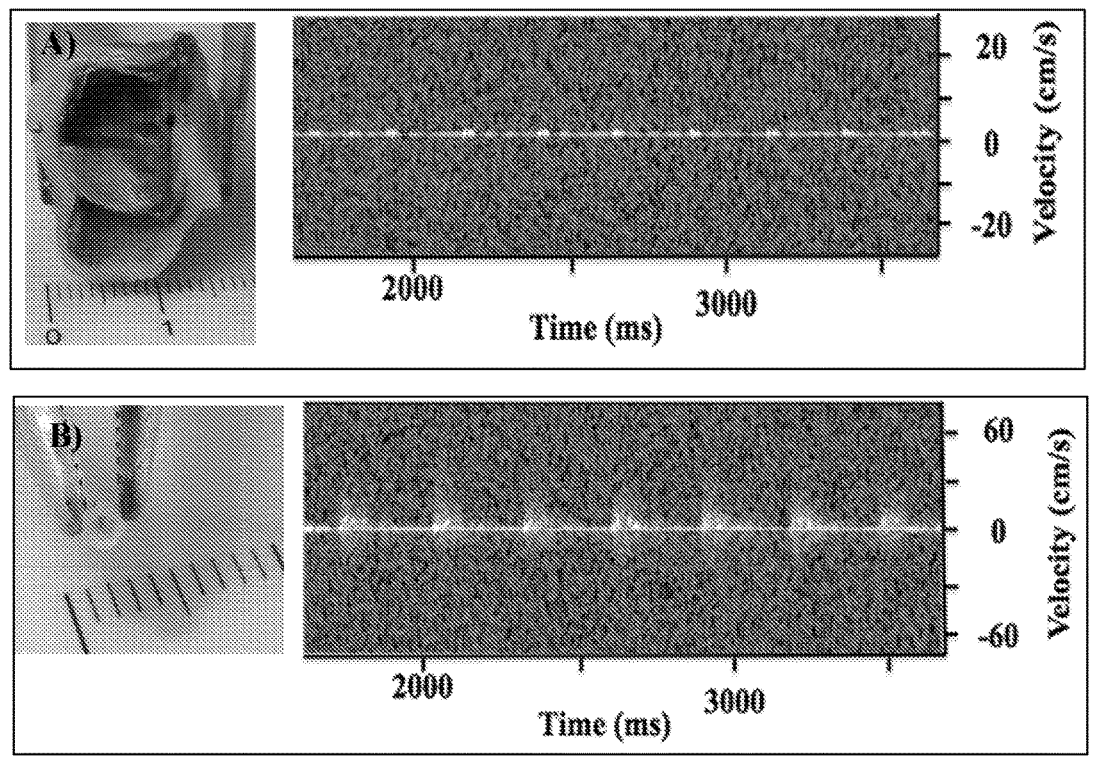
FIG. 15 is a panel of images showing explants and Doppler ultrasound imaging assessment of graft patency at week 4. Top panel is the control decellularized rat aorta and the bottom panel is the Hyaluronic Acid coated decellularized rat aorta. Control implants showed no flow recording as per the Doppler ultrasound imaging where a flat line is indicative of the absence of flow. The picture of the explant shown a large fibrotic blood clot well formed in the center of the implant preventing any blood flow through the graft. The graft is also dilated to 20× its original size which indicates that the graft wall were probably week and a large anastomosis formation. On the other hand the Hyaluronic Acid coated rat decellularized aortas (bottom panel) Doppler recording shows the typical rat pulsatile flow indicative of healthy vascular flow and typical rat aorta flow readouts of 30 cm/s velocity peak. The explant picture shows the absence of luminal occlusions, clots and blockages and sown that the graft is within the implanted dimensions of 2 mm diameter indicating the absence of dilatation.
Figure 16:
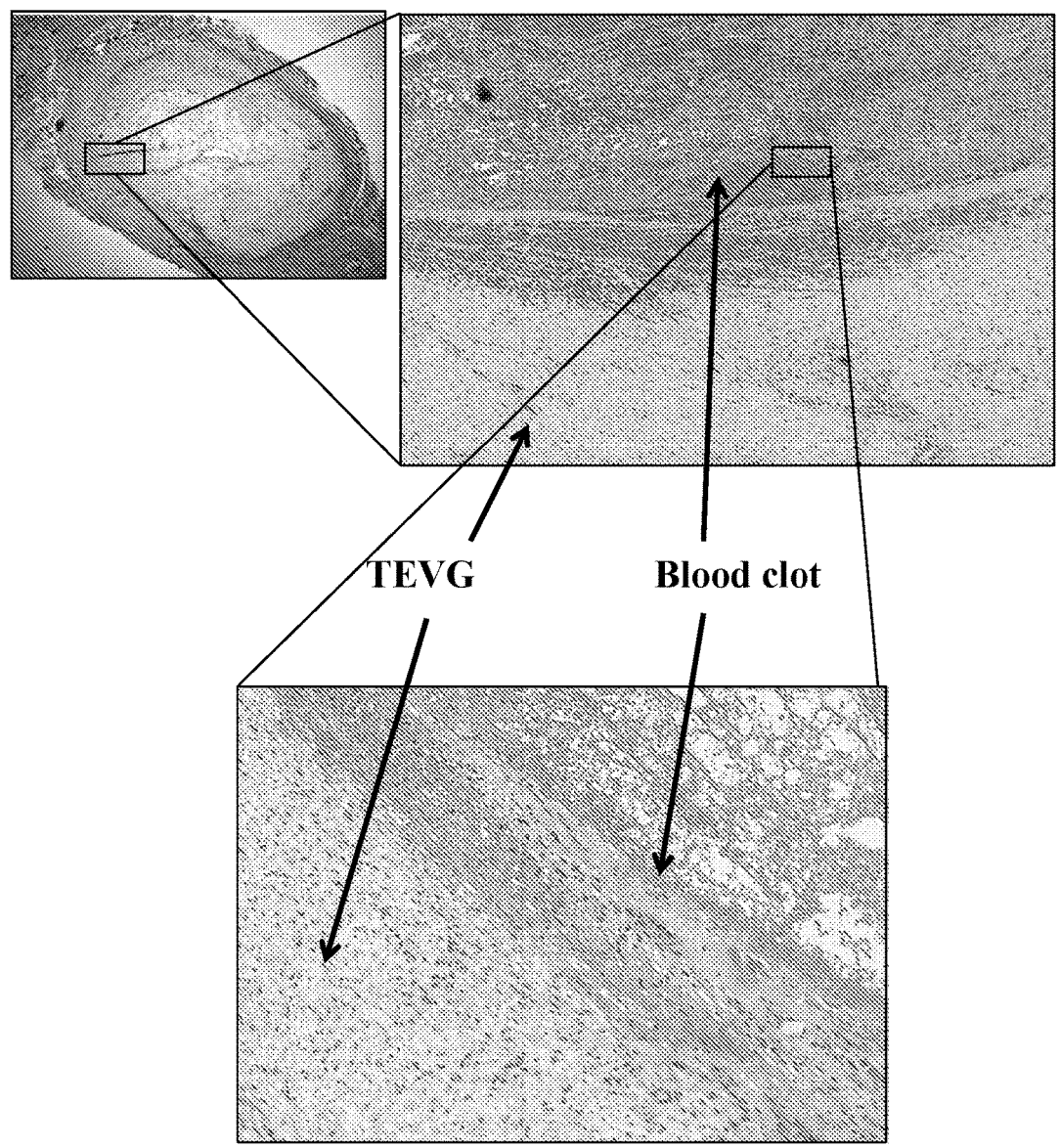
FIG. 16 is a panel of images showing cross-sections of TEVG-decellularized implanted end-to-side in dog carotid arteries at after 4 weeks of implantation. The top panel shows an example of the control group where the implanted graft was a decellularized TEVG without further modification. The bottom panel shown an example of Hyaluronic acid coated decellularized TEVG. All the sections were stained with hematoxylin and eosin (H&E). The absence of blood clots and occlusions is seen in the coated grafts and the deposition of endothelial cells is also visible on the Hyaluronic acid-heparin-coated grafts.

Similar to the rat animal model, the non-coated decellularized TEVG (control group) shown in FIG. 16 top panel formed large blood clots with large amounts of fibrin deposition and became almost fully occluded. The H&E stain in FIG. 15 showed the large fibrinized blood clot that was covering almost the entire luminal opening of the implanted graft. Hyaluronic acid-heparin-coated decellularized TEVG demonstrated variable results, with some areas showing total absence of blood clots and other areas showing some blood clot formation, but significantly less than the control grafts. Endothelial cells were found on the luminal surface of the Hyaluronic coated TEVG as identified in FIG. 16.

Hyaluronic acid coated decellularized TEVG implanted in the dog carotid artery animal model was a challenging model that further suggest clinical feasibility of hyaluronic acid coated vascular grafts.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising a substrate having at least one surface coated with an anti-thrombogenic coating, wherein the anti-thrombogenic coating comprises a first layer comprising a hydrogel and a second layer comprising an anti-coagulant, wherein the first layer contacts the substrate, and wherein the substrate is decellularized tissue.

2. The composition of claim 1, wherein the first layer comprises hyaluronic acid.

3. The composition of claim 2, wherein the hyaluronic acid is thiol-modified hyaluronic acid.

4. The composition of claim 1, wherein the first layer is crosslinked to the at least one surface of the substrate.

5. The composition of claim 1, wherein the second layer is crosslinked to the first layer.

6. The composition of claim 5, wherein the second layer comprises heparin.

7. The composition of claim 1, wherein the decellularized tissue is a decellularized blood vessel having a luminal surface, and wherein the anti-thrombogenic coating is coated on the luminal surface of the decellularized blood vessel.

* * * * *